(12) United States Patent
Mauer et al.

(10) Patent No.: US 9,698,062 B2
(45) Date of Patent: Jul. 4, 2017

(54) SYSTEM AND METHOD FOR PERFORMING A WET ETCHING PROCESS

(71) Applicant: VEECO PRECISION SURFACE PROCESSING LLC, Horsham, PA (US)

(72) Inventors: Laura Mauer, South Kent, CT (US); Elena Lawrence, East Norriton, PA (US); John Taddei, Breinigsville, PA (US); Ramey Youssef, Horsham, PA (US)

(73) Assignee: VEECO PRECISION SURFACE PROCESSING LLC, Horsham, PA (US)

( * ) Notice: Subject to any disclaimer, the term of this patent is extended or adjusted under 35 U.S.C. 154(b) by 5 days.

(21) Appl. No.: 13/780,657

(22) Filed: Feb. 28, 2013

(65) Prior Publication Data

US 2014/0242731 A1    Aug. 28, 2014

(51) Int. Cl.
| | | |
|---|---|---|
| *B44C 1/22* | (2006.01) | |
| *C23F 1/00* | (2006.01) | |
| *C03C 15/00* | (2006.01) | |
| *C03C 25/68* | (2006.01) | |
| *H01L 21/66* | (2006.01) | |
| *G01N 21/55* | (2014.01) | |
| *G06F 17/50* | (2006.01) | |
| *H01L 21/67* | (2006.01) | |

(52) U.S. Cl.
CPC ............ *H01L 22/12* (2013.01); *G01N 21/55* (2013.01); *G06F 17/50* (2013.01); *H01L 21/6708* (2013.01); *H01L 21/67046* (2013.01); *H01L 21/67051* (2013.01); *H01L 21/67253* (2013.01); *H01L 22/26* (2013.01); *H01L 2924/0002* (2013.01)

(58) Field of Classification Search
CPC .......... H01L 22/12; G01N 21/55; G06F 17/50
USPC ........................................... 216/84
See application file for complete search history.

(56) References Cited

U.S. PATENT DOCUMENTS

| | | | | |
|---|---|---|---|---|
| 6,123,865 | A  * | 9/2000 | Lin et al. ......................... | 216/91 |
| 2003/0084918 | A1 * | 5/2003 | Kim .................................. | 134/1.2 |
| 2005/0048800 | A1 * | 3/2005 | Wagener ........................ | 438/785 |
| 2006/0097355 | A1 * | 5/2006 | Bauer et al. ................... | 257/618 |
| 2006/0191637 | A1 * | 8/2006 | Zajac et al. ............... | 156/345.34 |
| 2008/0078427 | A1 * | 4/2008 | Matsunaga ....... | H01L 21/67051 134/33 |

(Continued)

*Primary Examiner* — Thomas Pham
(74) *Attorney, Agent, or Firm* — Leason Ellis LLP

(57) ABSTRACT

A system and method for performing a wet etching process is disclosed. The system includes multiple processing stations accessible by a transfer device, including a measuring station to optically measure the thickness of a substrate, a controller to calculate an etch recipe for the substrate, in real time, and cause a single wafer wet etching station to etch the substrate according to the recipe. In addition, the system can measure the after etch thickness and calculate etch recipes, in real time, as a function of the final measurements of a previous substrate. The system can also include an in situ end point detection device for detecting the TSV reveal point while etching TSVs substrates. The system provides an automated solution to adjust etch recipe parameters in real time according to feedback concerning previously etched wafers and precisely control the TSV reveal height and etch duration using end point detection.

17 Claims, 18 Drawing Sheets

(56) References Cited

U.S. PATENT DOCUMENTS

2008/0185103 A1    8/2008  Bornstein et al.
2012/0119355 A1*   5/2012  Chung et al. ................ 257/737
2012/0285482 A1   11/2012  Beck
2012/0285483 A1*  11/2012  Liu et al. .......................... 134/6

* cited by examiner

SYSTEM AND METHOD FOR PERFORMING A WET ETCHING PROCESS

TECHNICAL FIELD

The present invention generally relates to a system and method for etching semiconductor wafers for integrated circuits and, more specifically, relates to a system and method for etching semiconductor wafers (integrated circuit substrates) using a wet etching process that results in the etching of the wafer to a precise and uniform thickness.

BACKGROUND 2.5 and 3D Integration is becoming a reality in device manufacturing. A critical process step is the thinning of the silicon wafer to reveal the metal filled Through Silicon Via (TSV). Grinding is used to remove the bulk of the silicon wafer. Currently a multistep sequence of processes that includes chemical mechanical planarization (CMP) and plasma etching has been used to complete the final thinning of the silicon. However, this conventional process has a number of disadvantages associated therewith including but not limited to the complexity of the process and the associated costs. As described hereinafter, the present invention is directed at overcoming these deficiencies associated with the conventional process by providing a simple, cost effective method to wet etch the remaining silicon to reveal the TSVs.

TSV wafers (substrates) are manufactured by creating vias (holes) in the top surface of a substrate. These vias extend part way through the thickness of the wafer. The holes are then filled in with a conductive material, with or without an insulating liner. The bottom side of the wafer, opposite of where the vias were created, is then put through a grind process where mechanical grinding reduces the thickness of the substrate, effectively reducing the distance from the bottom of the via to the bottom surface of the substrate. Complete grinding of the substrate to expose the conductor is undesired as this would result in ions from the conductive material being smeared across the substrate surface, thereby altering the electrical properties at the contaminated sites and reducing yield. Any number of manufacturing steps can be performed on the top side of the wafer prior to further processing of the bottom side depending on the application. For example, for a device wafer, the full device structure and metallurgical components can be added to the top surface of the wafer. For 2.5D interposer applications, the top side wiring/interconnects can be completed. The wafer with vias is then typically mounted using an adhesive layer on a carrier wafer with the top of the wafer toward the carrier wafer.

The grinding process leaves a layer of substrate material above the vias that can be thicker at the edge, uniform across the wafer or thicker at the center of the wafer than at the edge (within wafer thickness variation). Likewise there can be a difference in height of the substrate material above the vias on a wafer to wafer basis (wafer to wafer thickness variation). These differences in the layer above the vias can be greater than the allowable difference in height of the exposed vias.

The carrier wafer and via wafer are mounted using an adhesive material. This adhesive layer can vary in thickness and uniformity, rendering exterior measurements ineffective at determining the thickness and uniformity of the material remaining in the top silicon wafer, above the end of the via.

Integrated circuit wafers, which typically are in the form of flat round disks (although other shapes are possible) and often are made from silicon, Gallium Arsenide, or other materials, may be processed using various chemicals. One process is the use of liquid chemical etchant to remove material from or on the substrate, this process is often referred to as wet etching. Commonly used methods include submerging the wafers in chemical baths (referred to as "batch processing" or "immersion processing"), or dispensing fluid on a wafer while spinning (referred to as "single wafer processing"). As wafer sizes increase and geometry sizes decrease, substantial benefits can be realized by employing single wafer processing inasmuch as the processing environment may be better controlled.

The etch rate of wet etch process will vary with changes in etchant concentration. The addition of small amounts fresh chemical etchant to sustain the etch rate is a common practice when the chemical etchant is recirculated. Typically the addition is based on a mathematical model based on wafers processed or elapsed time from etchant preparation. If there is no measurement feedback the etch rate will hold only as well as the mathematical model can predict the need to inject fresh chemical etchant. Likewise any external influences will not be accounted for and the etch rate will not remain constant. The depth of the etch process is a function of etch rate and time. Time is well controlled but the etch rate can vary based on several factors. Likewise the required depth to etch will vary as wafer to wafer there will be thickness variation. Accordingly the lack of a method to determine when the vias are exposed limits the capability to expose a precise depth on each wafer processed.

KOH (Potassium Hydroxide) is one etchant typically used because of its property to etch silicon selectively to conductors (such as Copper) and insulators (such as silicon oxide). After the KOH etch there remains residual Potassium on the surface of the wafer. The residual Potassium based particles and ions from the etch process will result in a change of electrical properties of the substrate surface that will result in yield loss if not removed after the etch process.

Similar to thinning TSV wafers, the conventional process for thinning non TSV wafers involves grinding to remove the bulk of the wafer and a multistep sequence of processes that includes chemical mechanical planarization (CMP) and plasma etching to complete the final thinning of the wafer. However, this conventional process has a number of disadvantages associated therewith including but not limited to the complexity of the process and the associated costs. As described hereinafter, the present invention is directed at overcoming these deficiencies associated with the conventional process by providing a simple, cost effective method to wet etch the remaining substrate to a desired thickness and surface uniformity.

Thus, there exists a need for a system and method for: (1) determining quantity and pattern of material to be removed from the substrate; (2) removing the material to the desired uniformity; (3) determining when to terminate the etch process in order to have exposed the vias to the desired depth and (4) cleaning up residual potassium from the TSV wafer surface without disturbing the exposed vias. The present invention achieves these objectives as described below.

SUMMARY OF THE INVENTION

According to a first aspect a system for performing a wet etching process is provided. The system includes a housing and a number of wafer/substrate processing stations disposed therein, including a measurement station which includes among other things an imaging device configured to measure an initial thickness information and a final thickness information for a substrate in real time. Also within the housing is an etching station that includes a single wafer wet etching device. An automated substrate transfer device is configured to controllably move the substrate between the measurement station and the single wafer wet etching station and any other stations included in the system. A computer implemented control system is communicatively coupled to the processing system and the stations therein. The control system is configured to control the wet etching process by causing the imaging device to measure the thickness of the substrate, and using that thickness information calculate an etch recipe for the substrate in real time. The controller also is configured to cause the single wafer wet etching device to etch the substrate according to the etch recipe, and, after the substrate is etched, cause the imaging device to re-measure the final thickness information. In addition, the control system can calculate, in real time, the etch recipe as a function of the final thickness information from a previous substrate.

In addition, the etching station can include an end-point detection device that can include a high intensity light emitter and detector and the control system can be configured to detect a reveal point for a substrate having TSVs using the information collected by the end-point detection device during the etching process. Moreover, the system can also include one or more cleaning stations within the housing and communicatively coupled to the control system to clean a substrate after the etching process. These and other aspects, features, and advantages of the system for performing a wet etching process can be appreciated from the processes and/or methods further described herein.

According to another aspect, a method for wet etching a substrate using a single wafer wet etching processing system is provided. The method includes measuring, at a measurement station, an initial thickness information for a particular substrate being processed. The initial thickness information includes a thickness of the substrate at one or more radial locations on the surface of the substrate and can be obtained by optically scanning the substrate using an imaging device disposed within the measurement station. The method also includes calculating an etch profile for the particular substrate according to the initial thickness information and according to the desired final etch profile which is the target physical characteristics of the substrate after processing. Calculating the etch profile can include calculating the radial thickness of the substrate and an etch depth. In addition, an etch recipe is generated for the particular substrate according to the calculated etch profile. The etch recipe includes settings for various parameters that control the execution of the wet etching process. The method also includes etching the particular substrate according to the etch recipe in order to achieve the desired final etch profile. It should be understood that the various stations used to perform this exemplary process are disposed within a housing of the processing system and are accessed by an automated substrate transfer device that is configured to controllably move the substrate between stations, thereby allowing measurements of the substrate in real-time as the substrate is undergoing etch processing. The method can also include the step of measuring final thickness information at the measurement station for the particular substrate after it has been etched. In addition, the final thickness information can be used to calculate the etch recipe for subsequently processed substrates.

The method can also include one or more steps for cleaning the particular substrate in a cleaning station disposed within the processing system. The method, in particular the etching step can also include the step of detecting the point in which one or more TSVs with a substrate are revealed using an end point detection device included within the etching station.

According to another aspect, A method for detecting an end point of an etching process in which a particular substrate having TSVs is being etched using a single wafer wet etching processing system is provided. The method includes emitting light onto at least a sample area of a surface of the particular substrate and detecting a reflection of the light off of the sample area of the surface. The method also includes calculating an intensity of the reflection and comparing the intensity to a reference intensity. The reference intensity is indicative of a reveal point, which is a point during the etching process at which the TSVs are revealed on the surface of the particular substrate (i.e., the etchant has removed the substrate layer above the TSVs to the point where the TSVs are exposed). The method includes detecting when the intensity corresponds to the reference intensity and thereby identifying the reveal point of the etching process. The method also includes setting an end point of the etching process in view of the identified reveal point and optionally in view an over etch duration which is inputted by a user. The end point can vary depending on the desired height According to another aspect, a computer implemented control system is provided for controlling a wet etching process of a substrate in a single wafer wet etching processing system. The single wafer wet etching processing system including a single wafer wet etching device and an imaging device disposed within a housing and accessible by an automated substrate transfer device and the control system including one or more processors communicatively coupled to the components of the processing system and configured to interact with a computer-readable storage medium and execute one or more software modules stored on the storage medium. The software modules include an imaging module configured to cause the imaging device to measure an initial thickness information for the substrate and receive the initial thickness information from the imaging device. The software modules also include a substrate thickness module configured to calculate, in real time, a radial thickness for the substrate and calculate an etch depth for the substrate according to at least the radial thickness information and the desired final etch profile. The software modules also include an etch recipe module configured to generate an etch recipe for the substrate according to the radial thickness and the etch depth and cause the single wafer wet etching device to etch the substrate according to the etch recipe. In addition, the imaging module can be further configured to, after the substrate is etched by the etch station, cause the imaging device to measure a final thickness information for the substrate, in real time, and receive the final thickness information from the imaging device. The system can also include an etch recipe module that is also configured to calculate the etch recipe according to final thickness information of a previous substrate. The system can also include a cleaning module configured to cause a substrate cleaning apparatus to clean the substrate.

According to another aspect, a computer implemented control system is provided for determining an end-point of a wet etching process of a substrate having TSVs by a single wafer wet etching station. The single wafer wet etching station including a single wafer wet etching device, a light emitter and a light detector, and the control system including one or more processors communicatively coupled to the single wafer wet etching device, the light emitter and the light detector and configured to interact with a computer-readable storage medium and execute one or more software modules stored on the storage medium. The software modules include an end-point detection module configured to cause the light emitter to emit a light onto at least a sample area of a surface of the substrate and cause the light detector to detect a reflection of the light off of the sample area of the surface. The endpoint detection module is also configured to calculate an intensity of the reflection and compare the intensity of the reflection to a reference intensity, wherein the reference intensity is indicative of a reveal point which is the point during the etching process at which the TSVs are revealed on the surface of the substrate. Using the compared intensity the control system can determine when the intensity corresponds to the reference intensity and set an end point of the etching process in view of the identified reveal point and optionally in view an over etch duration as defined by a user.

These and other aspects, features, and advantages can be appreciated from the accompanying description of certain embodiments of the invention and the accompanying drawing figures and claims.

DETAILED DESCRIPTION OF CERTAIN EMBODIMENTS OF THE INVENTION

FIGS. 1-5 illustrate a system 100 for performing a wet etching process in accordance with one embodiment of the present invention. The system 100 can thus be thought of as being a wet-etching facility for manufacturing semiconductor devices.

In a wafer wet treatment process of a semiconductor device manufacturing process, there are generally an etching process and a cleaning process as mentioned hereinbefore. A single wafer wet treatment apparatus used in an etching process dispenses chemical etchant in a controlled manner on a substrate for inducing a chemical reaction during a fixed time. It will be understood that the terms "wafer" and "substrate" are used interchangeably herein. A single wafer wet treatment apparatus used in a cleaning process causes a chemical solution to be dispensed onto a substrate and can also include a scrubbing device to mechanically scrub the substrate. Each of the wet treatment apparatuses can include a bath that collects fluids that overflow and discharge to an outer tank (or bath) or recirculate. The single wafer wet treatment apparatuses are further composed of conduits (e.g., pipes) which supply or discharge fluids (e.g, chemicals, water, solutions and the like) in the bath, and various kinds of control means for controlling fluid temperature or concentration and other process parameters as further described herein. The wafer wet treatment process can also include a measuring step whereby the wafers are measured for thickness.

In conventional systems for performing wet etching, there are a number of pieces of equipment that are used; however, there is generally a lack of integration between the pieces of equipment. More specifically, while the measurement step is performed at a first location, there is often the need for physically transferring the wafer to another remote station for the etching process using a wafer wet etching apparatus, and there is often a need for physically transferring the wafer to another remote station prior to completion of the etching process, for example, to clean the wafer or measure the wafer. This adds additional delay to the process since there can be wait times before reintroducing the wafer back to the wafer wet treatment apparatus. This conventional process is largely a manual process in which a technician manually moves the wafers between different pieces of equipment.

In direct contrast to the largely non-integrated conventional systems, the system 100 of the present invention is for the most part a largely or fully integrated system, thereby greatly reducing or eliminating unnecessary wait or down times, etc. between processing steps.

Figure 1:
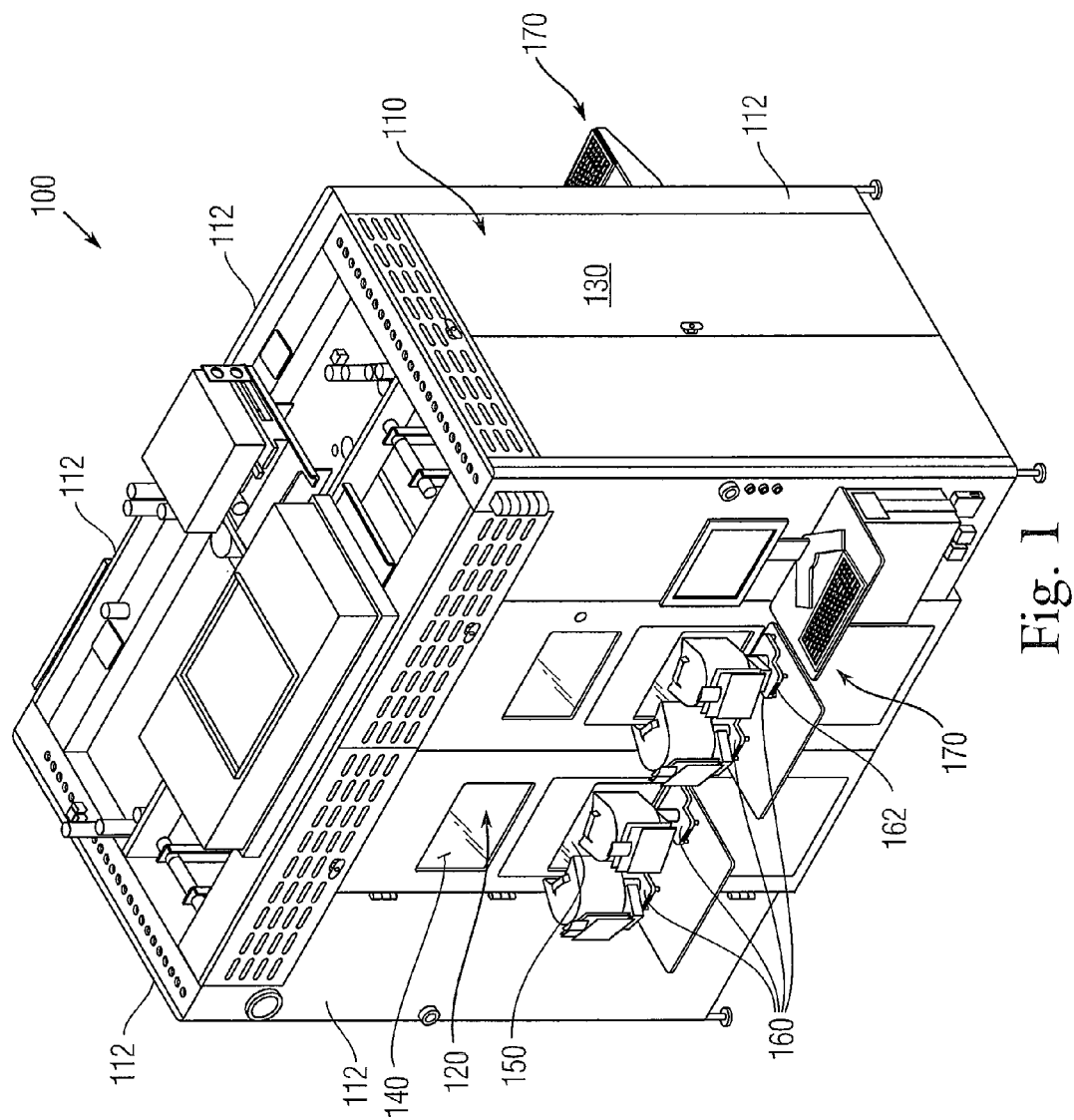
FIG. 1 is a perspective view showing a system for performing a wet etching process in accordance with one embodiment disclosed herein.
Figure 2:
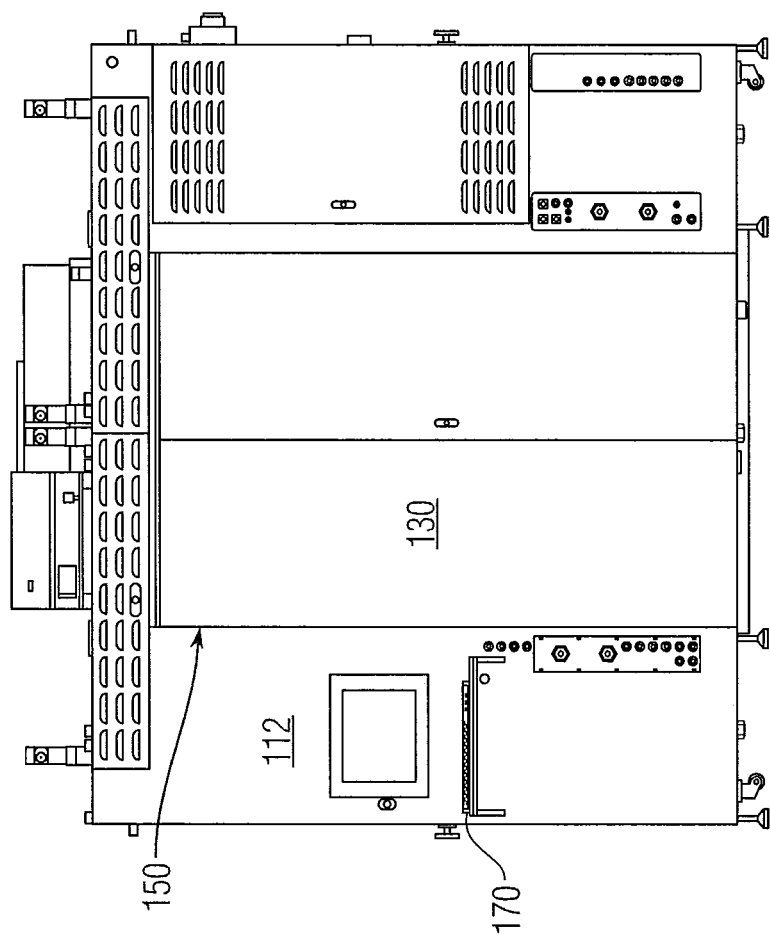
FIG. 2 is a front plan view showing a system for performing a wet etching process in accordance with one embodiment disclosed herein.

The system 100 is an integrated system that is defined by a number of different devices (equipment pieces) that are located at different stations within a housing 110. As shown in FIG. 1, the housing 110 is generally in the form of an upstanding cabinet or the like that has a plurality of walls 112 that define a hollow interior 120. The hollow interior 120 can be accessible through a number of different access points, including but not limited to a door assembly 130 shown at one end of the housing 110 and one or more side walls 112 can include windows 140 to allow direct access and viewing of the hollow interior 120 and more particularly, the equipment and processing stations included therein. In one embodiment, as illustrated, one side wall 112 can include transparent windows 140 and one or more access points 150. The opposite side walls 112 can include an access point 150 of a different form, such as a set of doors as shown in FIG. 2.

Each access point 150 can be in the form of an opening that provides an entrance into the hollow interior 120 and in addition, a wafer holding and loading device (loadport) 160 can be provided at such location along one side wall 112. The device 160 can be any number of conventional devices that are designed to hold and permit access to wafers contained therein and can be in the form of a FOUP loadport, with FOUP being an acronym for Front Opening Unified Pod or Front Opening Universal Pod. A FOUP is a specialized plastic enclosure with a cassette therein designed to hold silicon wafers securely and safely in a controlled environment, and to allow the wafers to be removed for processing or measurement by tools equipped with appropriate loadports and robotic handling systems. As illustrated in FIG. 1, the device 160 can be in the form of an input/output cassette device.

The wafer holding and loading device (loadport) 160 can be in the form of an input/output wafer cassette device which includes a housing which is configured to receive and hold a cassette holding a plurality of wafers. For example, the housing can include a door 162 at each end thereof, with one door 162 facing outwardly away from the hollow interior 120 so as to allow a technician to load one or more wafers, into the loadport 160. Another door 162 faces and is accessible within the hollow interior 120 so as to permit automated removal (and reloading) of the wafer from within the hollow interior 120 to allow the wafer to be transferred to the various stations contained within the hollow interior 120. The wafer holding and loading device 160 can be of the type that includes a plurality of racks or the like for holding a plurality of wafers in a vertically stacked manner.

The housing (cabinet) 110 can also include one or more computer terminals 170 which operate in the manner described below and allow the technician to both control and monitor the processing of the wafer within the housing 110 as the wafer is subjected to the various processing steps at the different stations.

It will also be appreciated that the system 100 can include a number of different conventional operating systems to provide for power, cooling, heating, fluid flow (plumbing architecture), etc. The system 100 also includes a number of different safety features including an emergency off button and audible and/or visual alarms to alert the technician when an abnormal condition is observed within the system 100.

Figure 3:
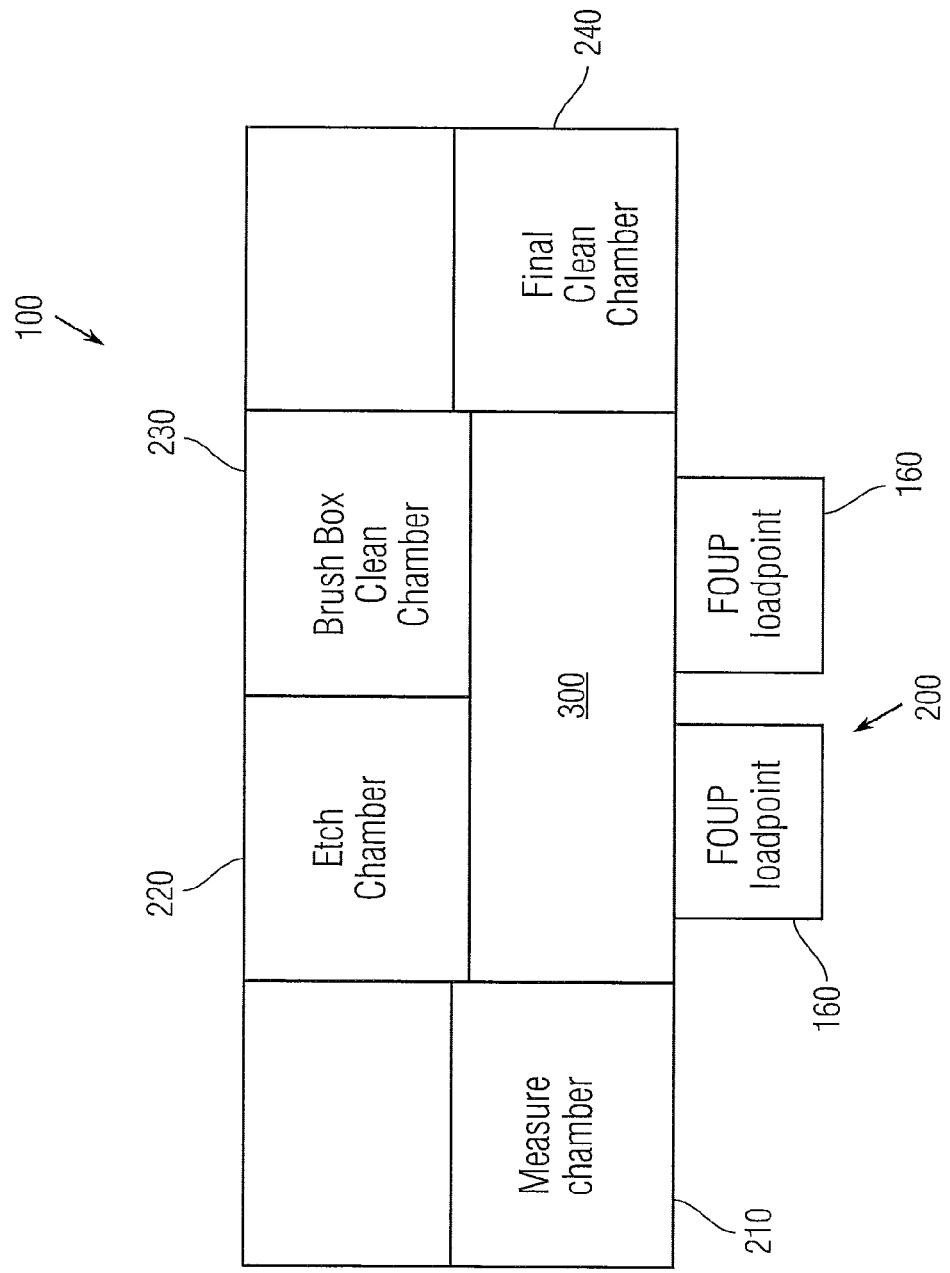
FIG. 3 is a block diagram showing an exemplary configuration of a system for performing a wet etching process in accordance with one embodiment disclosed herein.

FIG. 3 is a schematic view showing exemplary stations that are contained within the housing (cabinet) of the system of the present invention. In general, the system 100 includes a first station 200 that contains one or more devices 160 for holding wafers (e.g., FOUP loadports) and providing direct access to the interior 120 of the housing 110 as described above. A second station 210 is in the form of one or more measuring chambers for measuring different properties of the wafer as described below. A third station 220 contains one or more etch chambers for performing a single wafer wet-etching process on the wafer. A fourth station 230 and optionally also a fifth station 240 are cleaning chambers in which the processed wafer is cleaned. As a result of the system 100 being an automated system, a wafer transfer device 300 is provided and is configured to move one or more wafers from between the various stations of the system 100. The wafer transfer device 300 can take any number of different forms but generally is in the form of an automated device, such as a robot, that is configured to controllably grasp, move and release one or more wafers. Generally, the wafer transfer device 300 includes a robotic arm that has a grasp (holding) mechanism for grasping and holding a wafer and has a base about which the robotic arm can move in multiple directions (multiple degrees of freedom). It should be understood that one or more of the process stations/chambers can be combined to have multiple process functions. For example, the measuring apparatuses used in the measuring chamber can be incorporated into the wet etch chamber to provide a combined measuring and etch station. By way of further example, the etch chamber and cleaning chamber can be combined into multi-process chambers as would be understood by those skilled in the art.

Thus, the wafer transfer device 300 can thus be thought of as being an automated wafer handler. It will also be appreciated that the wafer transfer device is a computer operated device and therefore, as described below, operates in accordance with the execution of a software application, etc. In addition, it will also be appreciated that the wafer transfer device 300 can be operated in response to user generated commands, such as commands that are generated by the technician at a user interface, such as the computer terminal 170.

While in FIG. 3, the wafer transfer device 300 is shown as being centrally located within the interior of system 100, it is not limited to assuming such a position within the system so long as the wafer transfer device 300 is located at a position that allows the device 300 to access each of the stations of the system and transfer the wafer between all of the necessary stations.

Each of the individual stations mentioned above is described in greater detail below.

First Station 200

As mentioned above, the first station 200 includes one more wafer holding and loading devices (FOUP loadport or input/output cassettes) 160 for holding wafers in a sealed and secure manner. Any number of different conventional wafer holding and loading devices (FOUP loadport) 160 can be used in system 100. Typically, the wafer holding and loading device (FOUP loadport) 160 is of a type that contains a cassette holding the wafers. The door 162 is positioned such that the wafer transfer device (robot) 300 can directly access the wafers from the FOUP. The wafer holding and loading device (FOUP loadport) 160 can also include recognition features, such as RFID tag, barcode reader, etc. to allow it to be identified by readers on tools, etc. It should be understood that loadport 160 is not limited to being of an FOUP type. Various wafer holding and loading mechanisms can be used in addition to FOUPs having built in cassettes such as wafer boxes having removable cassettes as would be understood by those skilled in the art.

While FIG. 3 shows two blocks as constituting the station 200, it will be understood that this is only for illustrative purposes and is not limiting of the present invention since, as shown in FIG. 1, system 100 can include more than one wafer holding and loading device (FOUP loadport) 160. Moreover, it should be understood that each loadport 160 can be configured to receive one or more cassettes.

Second Station 210

As mentioned above, the second station 210 is a measuring station (wafer inspection station) in which a property of the wafer can be measured and in particular, the thickness of the wafer can be measured. The second station 210 thus includes a measuring device 600 for measuring one or more properties of a wafer. Any number of different types of measuring devices can be used. In accordance with one embodiment of the present invention, the measuring device 600 is in the form of an imaging device that is configured to measure one or more properties (e.g., wafer thickness and surface profile) of the wafer.

Figure 4:
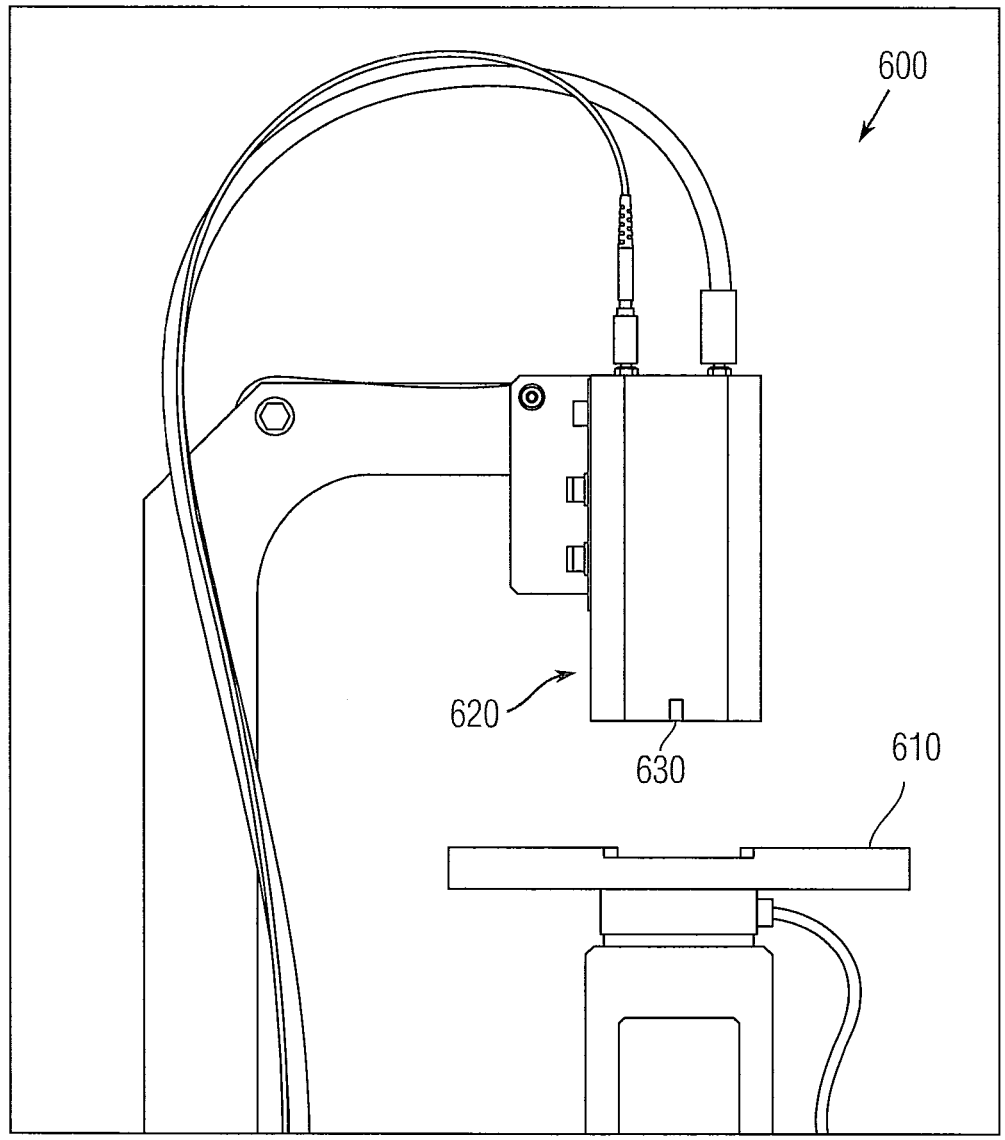
FIG. 4 is a front plan view showing a measurement station in accordance with one embodiment disclosed herein.

FIG. 4 shows one exemplary measuring (imaging) device 600 that includes a platform 610 for receiving and holding a wafer in a fixed orientation (e.g., in a horizontal orientation). The platform 610 can be of an adjustable type to accommodate different sized wafers. For example, the diameters of wafers can vary considerably and thus, the platform 610 is constructed to allow different sized wafers to be placed and supported thereon. In addition, the platform 160 can move in any number of different directions (x, y, z) (i.e., the platform 610 has multiple degrees of freedom of movement) and is rotatable such that the wafer can be rotated during the measuring process.

The imaging device 600 also includes a non-contact measurement component 620 that measures at least the thickness of the wafer and is also configured to detect (measure) and generate a surface profile for the wafer. The non-contact measurement component 620 includes imaging equipment and can be part of an automated device to allow movement of the component 620 with respect to the wafer on the platform 610. For example, the non-contact measurement component 620 can be in the form of an arm or the like that can move in any number of different directions (x, y, z) with respect to the wafer (i.e., the component 620 has multiple degrees of freedom of movement). Alternatively or in addition, the component 620 can be held in a stationary position and platform 610 supporting the wafer can be moved in any number of different directions (x, y, z) with respect to the component 620 and/or rotated.

The non-contact measurement component 620 includes one or more sensors 630, such as an optical sensor (e.g., an IR light sensor) and a light source that is directed at the surface of the wafer. The reflected light (after contacting the wafer) is collected by the imaging device and based on the collected information (and after processing thereof in accordance with execution of software), a number of different measurements of the wafer can be taken and recorded. More particularly, light is reflected at the top and bottom of each surface in the film stack (the layers of material that form the wafer) and the distance in reflected light is corrected according to the refractive index of the material in order to calculate depth. For example, the imaging device can measure the following properties (which is not an exhaustive list): wafer thickness; bow, warp, flatness; surface roughness; total thickness variation (TTV); optical inspection pattern recognition; and TSV depth, etc. One commercial source for one or more components of the imaging device is ISIS Sentronics gmbH, Germany however, other commercial sources are available.

The operation of the imaging device 600 is described in greater detail hereinafter.

In accordance with one aspect of the present invention and in direct contrast to conventional systems, the measuring station 210 is directly incorporated into and contained within the housing (cabinet) 110. As a result, the second station 210 and the imaging device 600 contained thereat is within reach of the wafer transfer device (robot) 300. This positioning allows the automated wafer transfer device 300 to easily move a wafer between the second station 210 and any of the other stations of the system 100. This is in direct contrast to conventional system in which measuring equipment is located at a remote location and requires wafers to be removed from the etch process in order for a measurement to be taken. After such measurement is taken, there is a wait period in which the wafer is held before being introduced back into the etch processing equipment. This leads to complexity and time delays, thereby directly and adversely impacting the number of wafers that can processed in a given time period. Moreover, in a production setting, these inefficiencies lead to batch processing of wafers, wherein multiple wafers are measured prior to being returned to the etch processing equipment. Accordingly any feedback regarding the etching process is only obtainable on a batch to batch basis and not in real time (i.e., on a wafer to wafer basis) thereby preventing the adjustment of process parameters in real time (on a wafer to wafer basis) and resulting in a decrease in quality and an increase in waste. Incorporating the measuring device into system 100 and implementing a process that includes a measuring step for each wafer before and after etching in a single wafer wet etch chamber as further described herein provides a system capable of tailoring the etch process parameters to the specific characteristics of each wafer and feedback concerning previously etched wafers in real time. Accordingly the system can achieve higher quality, minimize waste and the benefits generally associated with a single wafer wet etch process.

Third Station 220

The third station 220 is an etch station in which the wafer undergoes the single wafer wet etching process. As mentioned before, a single wafer wet etching process is generally performed by dispensing a certain amount of chemical etchant onto a wafer disposed within the station, and causing a chemical reaction with a contacted surface of the wafer so that the unnecessary portion of the contacted surface is etched by the chemical.

Figure 5:
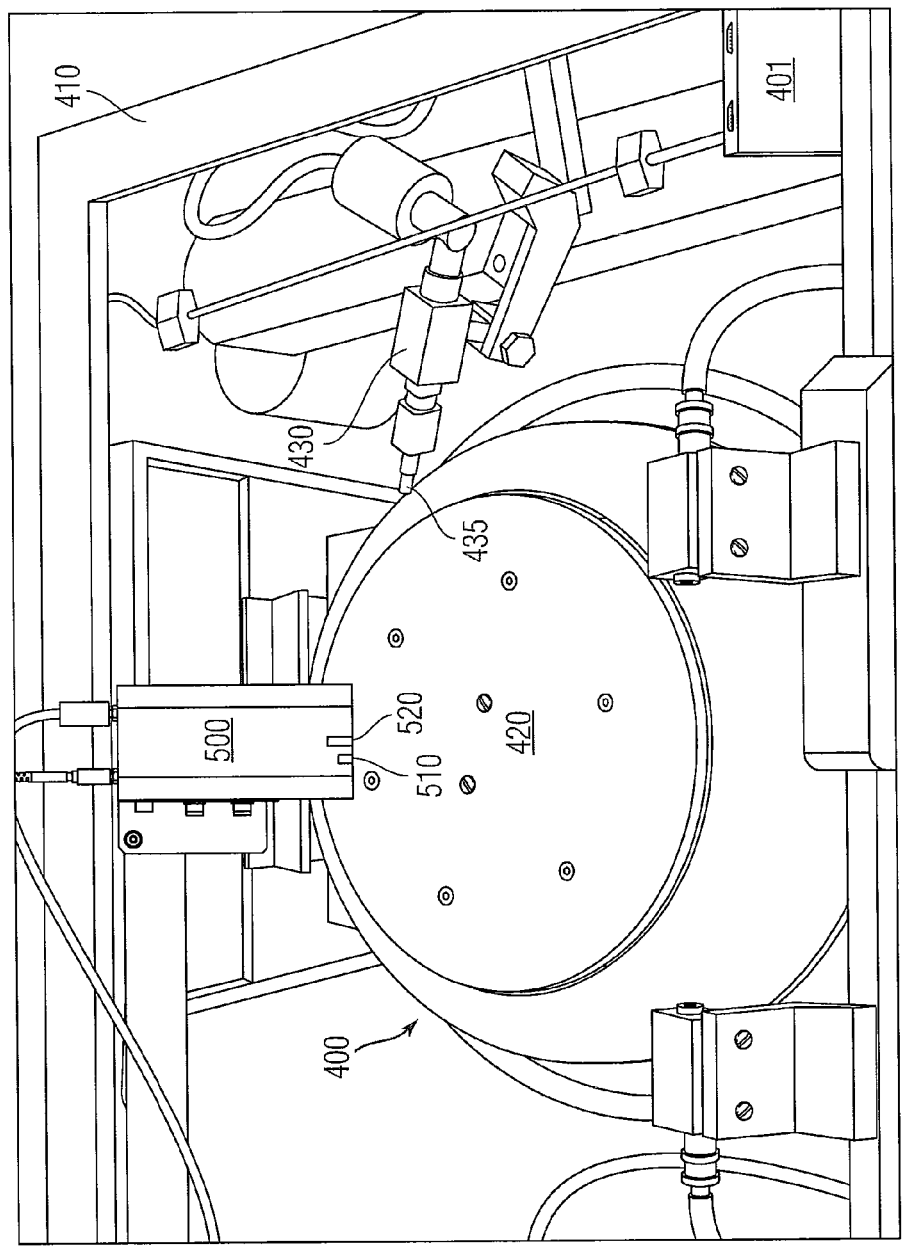
FIG. 5 is a perspective view showing a wet etching station in accordance with one embodiment disclosed herein.

As shown in FIG. 5, the third station 220 includes a single wafer wet etching apparatus 400 that includes an etch chamber (enclosure) 410 that contains the equipment and chemical etchant used in the wet etching process. The etch chamber 410 can thus be thought of as a chemical containment structure. It will be understood that third station can hold a plurality of etching apparatus' 410, such as is a vertically stacked orientation, to allow wet etching to be performed simultaneously on more than one wafer. The enclosure 410 also collects and contains the chemicals used in the etching process.

The wet etching apparatus 400 located at the third station 220 also includes spin chuck 420 (variable speed controlled by an etch controller 401 which is part of the overall process control system described herein) on which the wafer rests, as well as an etch tool (arm) 430 that includes one or more nozzles (orifice) 435 that dispenses a fluid (e.g., one or more liquids, preferably the chemical etchant). The etch tool 430 can be in the form of an arm that is movable along multiple directions (x, y, z directions) and thus, has multiple degrees of freedom. The etch tool 430 is a controllable tool in that it is controlled by a computing device such as etch controller 401 and is part of the overall programmable computer system employed in the system 100 as described herein. As a result, the etch tool 430 can be driven to any specific location of the wafer, etc.

The wet etching apparatus 400 also includes a fluid delivery and fluid removal system for both introducing the etch chemicals and removing such chemicals from the chamber. These components are implemented using a conventional fluid plumbing scheme in which conduits are provided for supplying fluid (e.g., one or more liquids, preferably a chemical etchant) to the nozzle 435. In addition, the wet etching apparatus 400 includes conduits and mechanisms for discharging fluid(s) that accumulate within the enclosure 410 during the wet etching process.

The mechanical chuck 420 permits the chuck 420 to hold the wafer: The chuck 420 includes a main shaft (not shown) which can be joined to a driving shaft of a motor so as to allow the wafer held by the spin chuck 420 to make a spin rotation about a Z-axis. A power source switch of the motor is connected to an output side of the etch controller 401, with the result that the rotation speed of the motor is controlled by the controller 401. Also, the spin chuck 420 can be supported by a lift mechanism (not shown) so as to be movable in a direction of the Z-axis.

Traditionally, around the outer periphery and bottom portion of the spin chuck 420 a structure is provided for receiving and collecting the etchant solution, which is centrifugally separated from the wafer and is then discharged to the outside. Part of the mechanism for discharging fluid(s) from the enclosure 410 can be an exhaust gas passageway and drain pipes that are formed in the bottom portions of the collector structure that surrounds the chuck 420. The liquid stored in the collector structure can be discharged to the outside through one or more drain pipes or recirculated.

In accordance with the present invention, any number of suitable etching solutions can be used so long as they are suitable for a wet etching process and for the intended substrate and application. Thus, different chemistries can be used based on a number of different parameters, including in view of the properties of the wafer.

With respect to the delivery of the etchant solution, the wet etching apparatus 400 also includes means for controlling the flow properties (flow rate) and temperature of the etchant solution. The operating system can include one or more first flow rate control sections, including but not limited to a pump or valve, that extend from a liquid supply source to a nozzle. The operating section of the flow rate control section can be connected to the output side of the etch controller 401 so as to control the flow rate of the etchant solution supplied to the nozzle. In addition, other control mechanism can be used to control the concentration of the etchant solution. The control of the concentration of the etchant is one means for controlling the overall etch rate and etch process for a given wafer.

In accordance with one aspect of the present invention, the wet etching apparatus 400 includes an end point detection device 500. One exemplary end point detection device 500 includes a light emitter 510 (e.g., a high intensity white light emitter) and a light detector 520 (e.g., charge-coupled device (CCD) detector). It will be appreciated that the light emitter 510 can have different constructions depending upon the particular applications in which it is used and in one embodiment, the light emitter is a high intensity white light emitter with a red filter. The operation of the end point detection device 500 is described in greater detail hereinafter; however, the device 500 is responsive to a computing device, such as etch controller 401 or computing device 170, and the light emitting device 510 emits light (e.g., white light) onto at least a portion of the surface of the particular wafer in the wet etching station 220. The light detector 520 (e.g., CCD detector) detects the light being reflected by the portion of the particular wafer and the CCD detector 520 transmits the detected light information to a process control system as further described herein. As described herein, the end point detection device 500 is advantageously employed by the present invention to expose via materials to a precise and uniform depth. It will be appreciated that the device 500 is not limited to being formed of the above pieces of equipment but in generally is an optics based system in which light characteristics are analyzed in order to determine a property or condition of the substrate.

Fourth and Fifth Stations 230, 240

After the wafer undergoes processing at the etch station 220, the wafer is then cleaned at one or more wafer cleaning stations. FIG. 3 shows two distinct cleaning stations 230, 240; however, this is merely representative of one embodiment and it will be appreciated that a single cleaning station can be used. In such a construction, the single cleaning station can still employ one or more different cleaning techniques for cleaning the wafer.

Figure 6A:
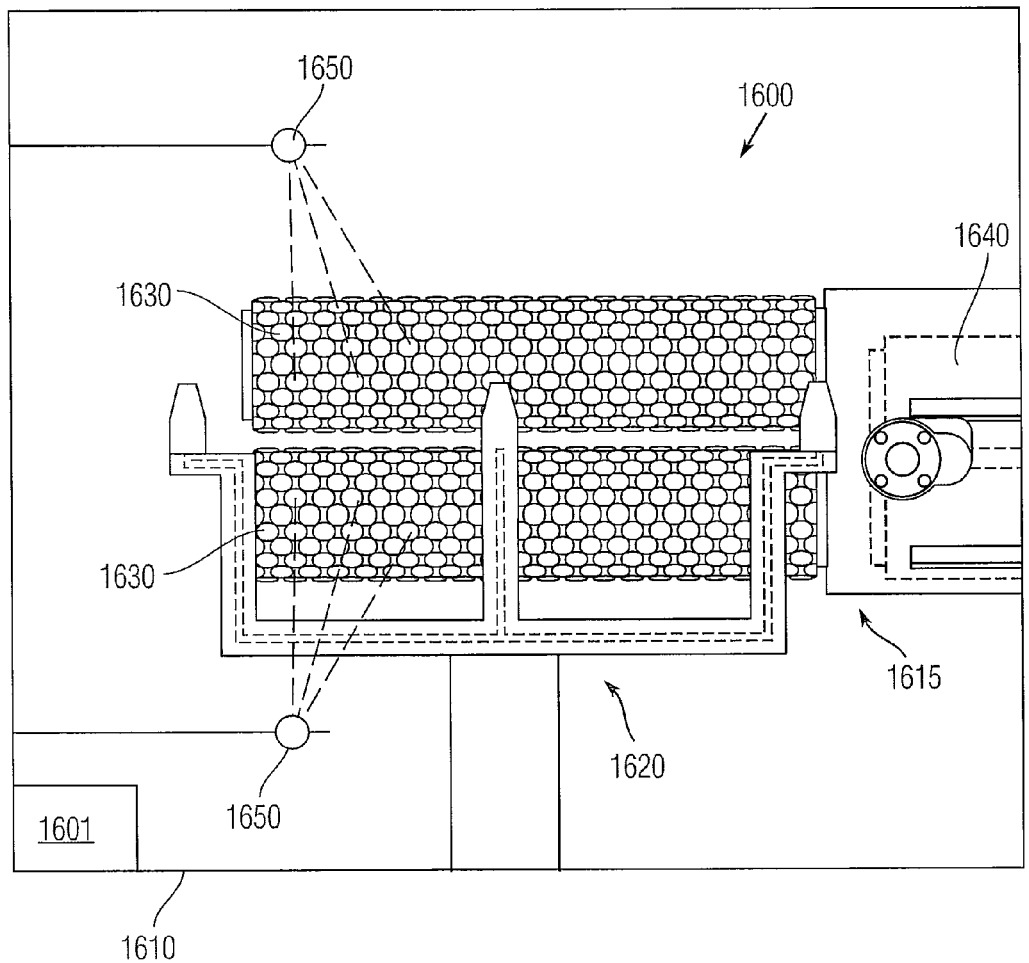
FIG. 6A is a front plan view showing a cleaning station in accordance with one embodiment disclosed herein.

As shown in FIG. 6A, the cleaning station 230 can be of a wafer cleaning apparatus 1600 (of the scrubbing or brush box type) in which the wafer is scrubbed while a cleaning solution is dispensed on the wafer to remove larger residual particles and etch residue. More specifically, the wafer cleaning apparatus 1600 can include a chamber (enclosure) 1610 that contains the equipment and contains the injected cleaning solution used in the cleaning process. The chamber thus at least partially is a sealed environment and can include a wafer scrubbing device 1615 which comprises a chuck 1620 (e.g., spin, rotating chuck) for supporting a wafer to be cleaned. The wafer scrubbing device also comprises a brush mechanism which includes one or more brushes 1630 for scrubbing the wafer. The brush mechanism also includes a drive mechanism 1640 for rotating the brushes, a clamping mechanism for clamping and unclamping the brushes, and a motor for driving the brushes, according to one or more controlled directions (e.g., radially) across the surfaces of the wafer.

During an exemplary scrubbing process, it is desirable to direct streams of water or streams of a cleaning solution at both surfaces of the spinning wafer to wash away particulates. This is typically accomplished by providing spray nozzles 1650 positioned above and/or below the wafer. The spray nozzles are preferably connected to a source of pure water or cleaning solution through supply pipes. The flow rate of the water or cleaning solution can be controlled by a pump and valve arrangement (not shown) which is, in turn, controlled by a cleaning controller 1601 (which is part of the overall process control system described herein). Alternatively, a pressurized fluid source can be used to provide fluid flow.

The cleaning station 240 can be a physically different station that is located proximate to the cleaning station 230 and is of a type in which the wafer is subjected to a different cleaning process than the one employed in the cleaning station 230. The cleaning station 240 can be thought of as being a final clean station. As mentioned above, the first cleaning step involves a scrubbing process which primarily removes the larger particles and residual etchant. The wafer can be transferred wet from the first cleaning station 230 to the final cleaning station 240.

Figure 6B:
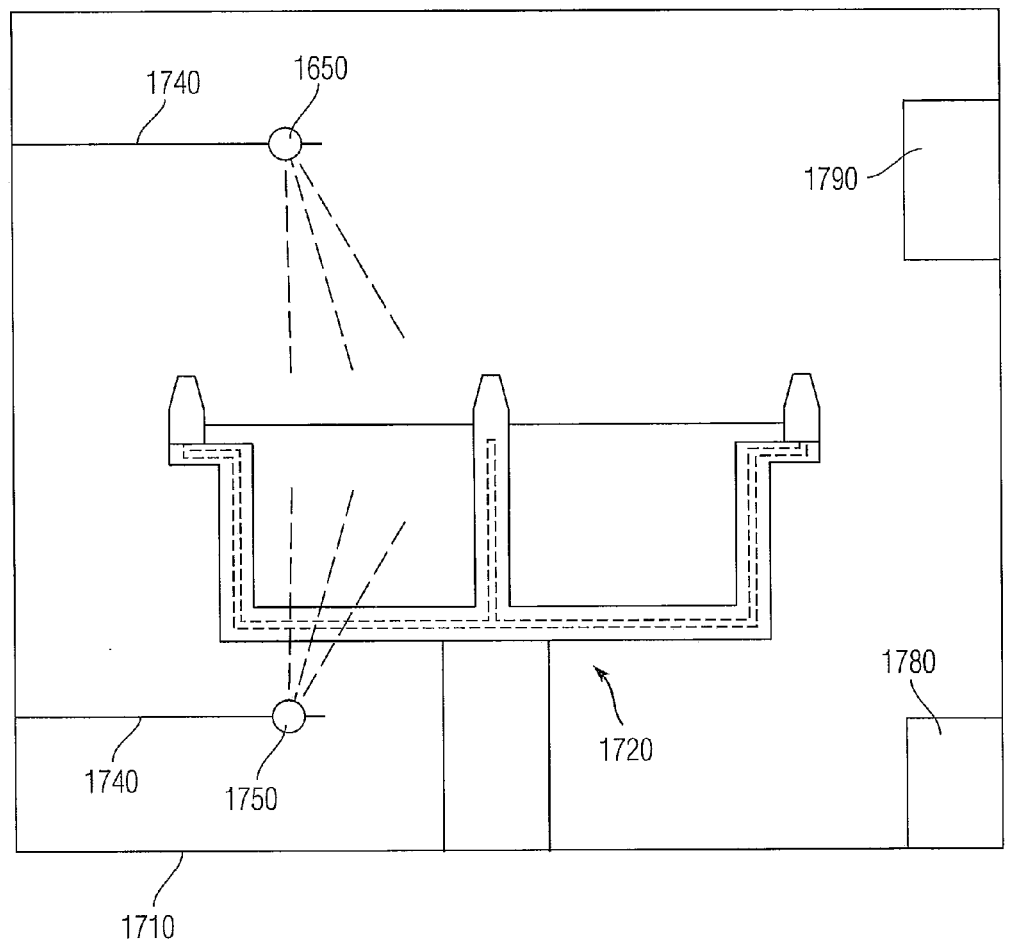
FIG. 6B is a front plan view showing a cleaning station in accordance with one embodiment disclosed herein.

As shown in FIG. 6B, similar to cleaning station 230, the final cleaning apparatus 1700 can be in the form of a chamber 1710 and includes one or more arms 1740 and nozzles 1750 to dispense a high velocity spray onto the wafer and/or use a megasonic cleaning apparatus 1780 for the removal of small particles from the wafer surface. In addition, station 240 can include a drying apparatus 1790 to dry the wafer at the end of the final cleaning process.

The Wet Etch Process using System 100

Figure 7A:
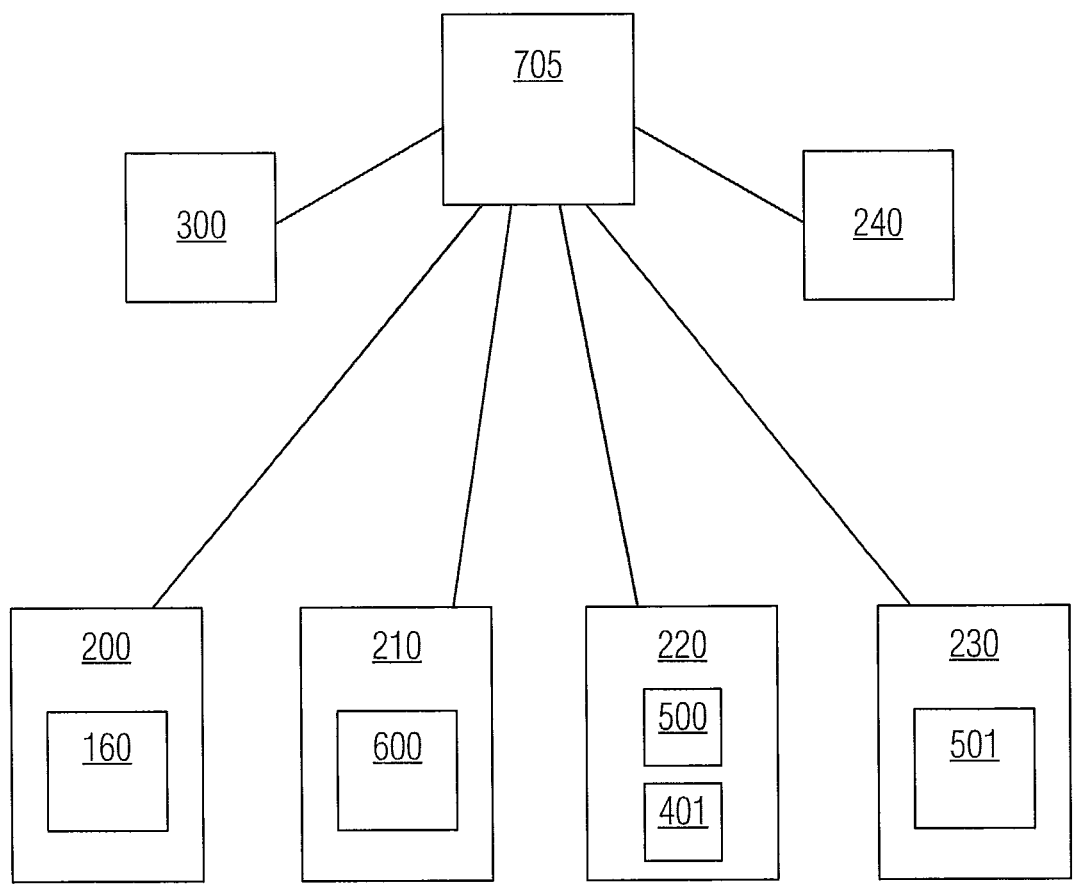
FIG. 7A is a block diagram showing an exemplary configuration of a system for performing a wet etching process in accordance with one embodiment disclosed herein.

FIG. 7A is a high-level diagram illustrating an exemplary configuration a process control system 700 for use with the system 100 for performing a wet etching process. In one arrangement, the process control system consists of one or more computing devices including a process controller 705. It should be understood that process controller 705 can be practically any computing device and/or data processing apparatus capable of embodying the systems and/or methods described herein.

Process controller 705 can be configured to communicate with the various computer-controlled components of the system 100, including first station 200, second station 210, third station 220, fourth station 230, fifth station 240, and the computer controlled devices or controllers associated therewith including but not limited to wafer transfer device 300, FOUP loadports 160, imaging device 600, etch controller 401, end point detection device 500 and cleaning controller 1601 transmitting electronic information to and receiving electronic information from the various components.

It should be noted that while FIG. 7A depicts the process control system 700 with respect to a process controller 705, it should be understood that any number of process controllers can interact with the process control system 700 and the constituent computer controlled components of system 100 in the manner described herein. It should be further understood that while the various computing devices and machines referenced herein, including but not limited to computer terminal 170, process controller 705, first station 200, second station 210, third station 220, fourth station 230, fifth station 240, and the computer controlled devices or controllers associated therewith including but not limited to wafer transfer device 300, FOUP loadports 160, imaging device 600, etch controller 401, end point detection device 500 and cleaning controller 1601 are referred to herein as individual/single devices and/or machines, in certain implementations the referenced devices and machines, and their associated and/or accompanying operations, features, and/or functionalities can be arranged or otherwise employed across any number of devices and/or machines, such as over a direct connection or network connection, as is known to those of skill in the art.

Figure 7B:
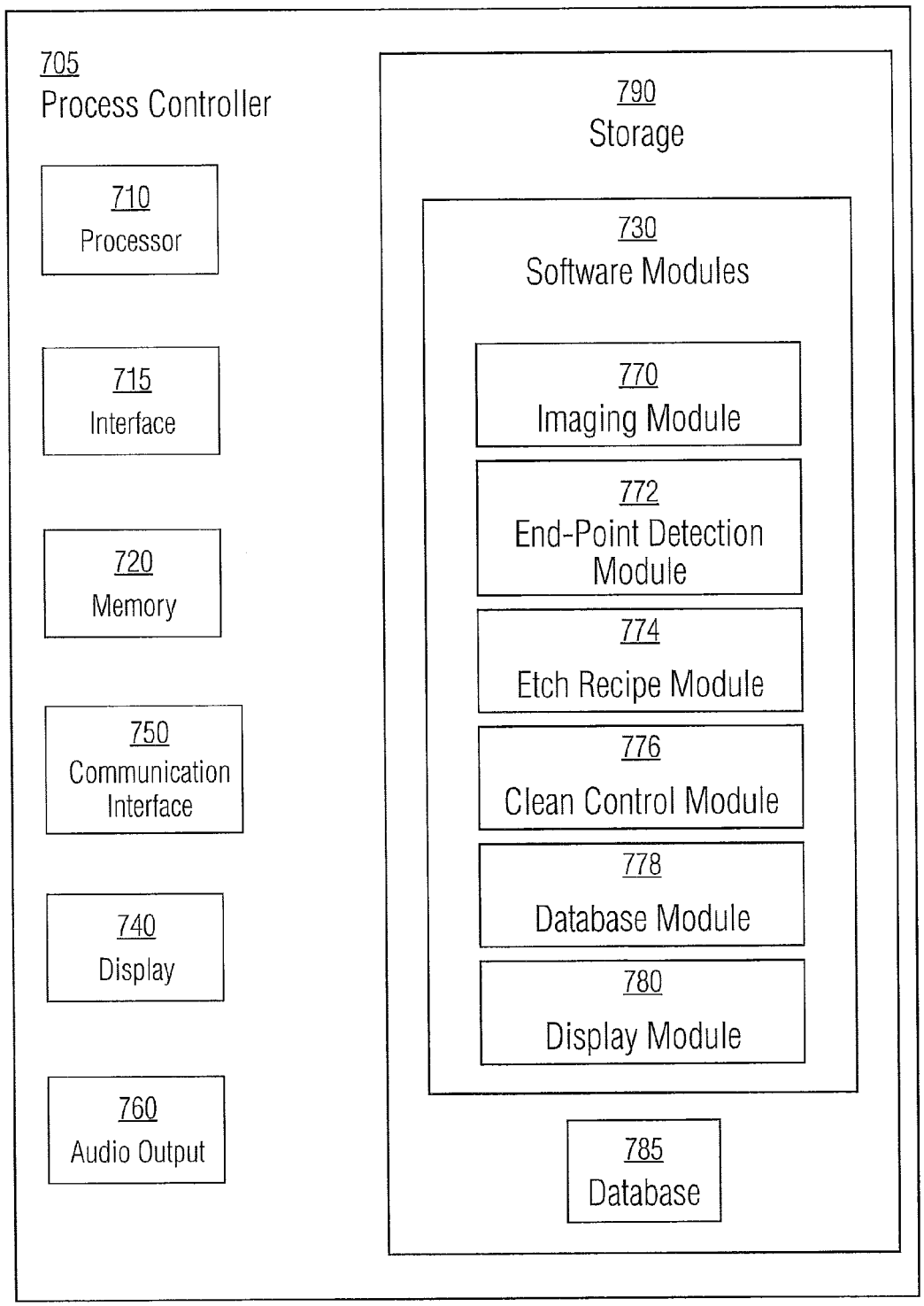
FIG. 7B is a block diagram showing an exemplary configuration of a process control system in accordance with one embodiment disclosed herein.

FIG. 7B is a block diagram illustrating an exemplary configuration of process controller 705 of the system 100 for performing a wet etching process. Process controller includes various hardware and software components that serve to enable operation of the system, including a processor 710, memory 720, display 740, storage 790 and a communication interface 750. Processor 710 serves to execute software instructions that can be loaded into memory 720. Processor 710 can be a number of processors, a multi-processor core, or some other type of processor, depending on the particular implementation.

Preferably, memory 720 and/or storage 790 are accessible by processor 710, thereby enabling processor to receive and execute instructions stored on memory and/or on storage. Memory can be, for example, a random access memory (RAM) or any other suitable volatile or non-volatile computer readable storage medium. In addition, memory can be fixed or removable. Storage 790 can take various forms, depending on the particular implementation. For example, storage can contain one or more components or devices such as a hard drive, a flash memory, a rewritable optical disk, a rewritable magnetic tape, or some combination of the above. Storage also can be fixed or removable.

One or more software modules 730 are encoded in storage 790 and/or in memory 720. The software modules can comprise one or more software programs or applications having computer program code or a set of instructions executed in processor 710. Such computer program code or instructions for carrying out operations for aspects of the systems and methods disclosed herein and can be written in any combination of one or more programming languages. The program code can execute entirely on process controller 705, as a stand-alone software package, partly on process controller, or entirely on another computing/device or partly on another remote computing/device. In the latter scenario, the remote computing device can be connected to process controller through any type of direct electronic connection or network, including a local area network (LAN) or a wide area network (WAN), or the connection can be made to an external computer (for example, through the Internet using an Internet Service Provider).

Preferably, included among the software modules 730 is an imaging module 770, an end point detection module 772, an etch recipe module 774, a clean control module 776, and a database module 778 and display module 780 that are executed by processor 710. During execution of the software modules 730, the processor configures the process controller 705 to perform various operations relating to the system 100 for performing a wet etching process, as will be described in greater detail below.

It can also be said that the program code of software modules 730 and one or more computer readable storage devices (such as memory 720 and/or storage 790) form a computer program product that can be manufactured and/or distributed in accordance with the present invention, as is known to those of ordinary skill in the art.

It should be understood that in some illustrative embodiments, one or more of software modules 730 can be downloaded over a network to storage 790 from another device or system via communication interface 750 for use within the system 100. In addition, it should be noted that other information and/or data relevant to the operation of the present systems and methods (such as database 785) can also be stored on storage, as will be discussed in greater detail below.

Also preferably stored on storage 790 is database 785. As will be described in greater detail below, database contains and/or maintains various data items and elements that are utilized throughout the various operations of the system 100. The information stored in database can include but is not limited to, parameter adjustment algorithms, recipes, chemical mixture details, set-points, settings, alarms, actual values for process variables, and historical data collected and analyzed by the process controller (e.g, batch records, substrate thickness measurement information, via depth measurement information) as will be described in greater detail herein. It should be noted that although database is depicted as being configured locally to process controller 705, in certain implementations database and/or various of the data elements stored therein can be located remotely (such as on a remote computing device or server—not shown) and connected to process controller through a network or in a manner known to those of ordinary skill in the art.

An interface 715 is also operatively connected to the processor 710. The interface can be one or more input device(s) such as switch(es), button(s), key(s), a touchscreen, microphone, etc. as would be understood in the art of electronic computing devices. Interface serves to facilitate the capture of commands from the user such as on-off commands or settings related to operation of the system 100.

Display 740 is also operatively connected to processor 710. Display includes a screen or any other such presentation device which enables the user to view information relating to operation of the system 100 including control settings, command prompts and data collected by various components of the system 100 and provided to process controller. By way of example, display can be a digital display such as a dot matrix display or other 2-dimensional display.

By way of further example, interface and display can be integrated into a touch screen display. Accordingly, the screen is used to show a graphical user interface, which can display various data and provide "forms" that include fields that allow for the entry of information by the user. Touching the touch screen at locations corresponding to the display of a graphical user interface allows the person to interact with the device to enter data, change settings, control functions, etc. So, when the touch screen is touched, interface communicates this change to processor, and settings can be changed or user entered information can be captured and stored in the memory.

Audio output 760 is also operatively connected to the processor 710. Audio output can be any type of speaker system that is configured to play electronic audio files or generate audio tones as would be understood by those of ordinary skill in the art. Audio output can be integrated to the process controller 705 or external to the process controller 705.

Communication interface 750 is also operatively connected to the processor 710 and can be any interface that enables communication between the process controller 705 and external devices, machines and/or elements including [robot, imaging device, etch controller, clean controller, chemistry controller]. Preferably, communication interface includes, but is not limited to, Ethernet, IEEE 1394, parallel, PS/2, Serial, USB, VGA, DVI, SCSI, HDMI, a Network Interface Card (NIC), an integrated network interface, a radio frequency transmitter/receiver (e.g., Bluetooth, cellular, NFC), a satellite communication transmitter/receiver, an infrared port, and/or any other such interfaces for connecting process controller 705 to other computing devices and/or communication networks such as private networks and the Internet. Such connections can include a wired connection (e.g. using the RS232 standard) or a wireless connection (e.g. using the 802.11 standard) though it should be understood that communication interface can be practically any interface that enables communication to/from the process controller 705.

At various points during the operation of the system 100 for performing a wet etching process, process controller 705 can communicate with one or more computing devices, for instance, computing devices used to operate the various process stations and constituent devices as will be further described in greater detail herein. Such computing devices can transmit and/or receive data to/from process controller 705 and between one another, thereby preferably initiating maintaining, and/or enhancing the operation of the system 100, as will be described in greater detail below.

The operation of the system 100 for performing a wet etching process and the various elements and components described above will be further appreciated with reference to the process for exposing TSVs as described below, in conjunction with FIGS. 7, 8, 9A-9I and 10, 11.

Figure 8:
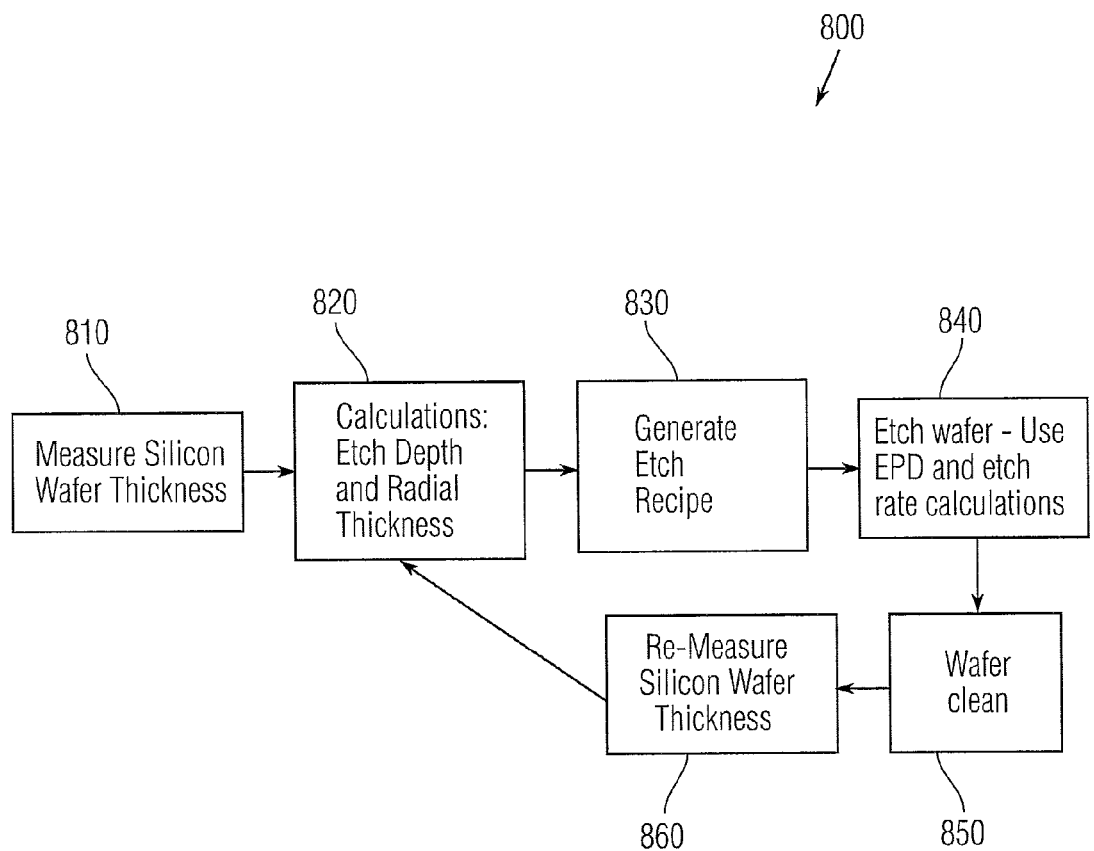
FIG. 8 is a flow diagram showing a routine for performing a wet etching process in accordance with at least one embodiment disclosed herein.

FIG. 8 is a flowchart illustrating a process flow 800 for etching wafers using system 100 in accordance with an embodiment of the invention. It should be understood that the exemplary process can be performed on post grind TSV substrates (i.e., wafers) in which the TSVs are not exposed on the top surface of the substrate due to a layer of overburden. Moreover, the bottom surface of the substrate is mounted to a carrier with an adhesive layer that can vary in thickness from one substrate to another. However, it should be understood that substrates are not limited to this particular carrier configuration as the exemplary process is operable on substrates in alternative carrier configurations and non-carrier configurations as would be understood by those skilled in the art. The exemplary process provides specialized metrology to determine the thickness of the overburden and wet etch substrates using the system 100 to expose the TSVs to a desired depth and substrate surface uniformity. Although process flow is generally discussed in relation to TSV substrates, it should be understood that the exemplary process can be performed on non-TSV substrates and provides specialized metrology to determine the thickness of the substrate and wet etch non-TSV substrates using system 100 to a desired thickness and substrate surface uniformity.

In process block 810, the system 100 measures the thickness of a particular substrate. In process block 820, the system calculates the etch depth and radial thickness for the particular substrate in accordance with the thickness measurements taken in process block 810. In process block 830, the system generates an etch recipe for the particular substrate to achieve the desired etch profile for the particular substrate. In process block 840, the system etches the particular substrate according to the etch recipe. The step of etching the particular substrate in process block 840 can further incorporate an end point detection process as further described herein. In process block 850, the system cleans the substrate to remove any residual particles, ions and etchant. In process block 860, the system measures the thickness of the particular substrate and provides the thickness measurements to the process controller to analyze the physical properties of the substrate, evaluate the efficacy of the etch recipe, and adjust the etch recipe for subsequent substrates being put through process flow 800 accordingly.

The specific steps followed in each process block will be described in further detail in conjunction with FIGS. 7A-B, 8, 9A-9I and 10-11. It should be appreciated that more or fewer operations can be performed than shown in the figures and described herein. These operations can also be performed in a different order than those described herein, combined into multi step processes or broken into sub-routines. The steps are described in the context of system 100 however practice of the steps is not limited to the exemplary configuration of system 100 as described in FIGS. 1-7.

Figure 9A:
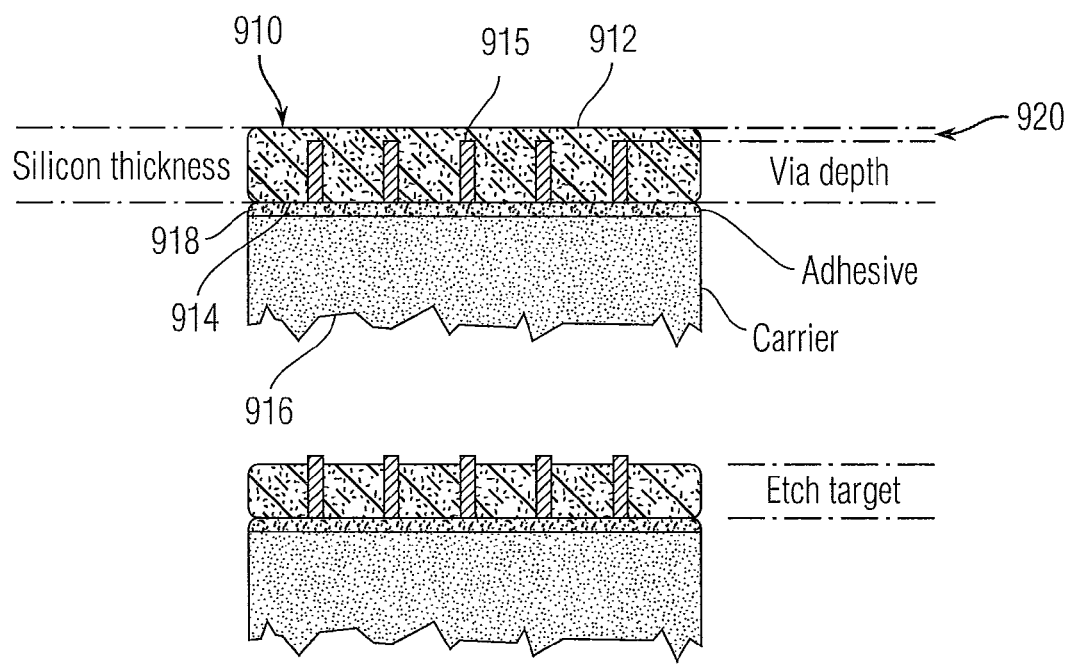
FIG. 9A is a cross-section view showing an exemplary silicon substrate having TSVs in accordance with one embodiment disclosed herein.

The process begins at block/step 810, where processor 710 executing one or more of software modules 730, including, preferably imaging module 772, configures process controller 705 to cause imaging device to collect thickness information for a particular substrate. FIG. 9A depicts a cross section of an exemplary post grind TSV substrate 910 prior to revealing the TSVs. The substrate includes a top surface 912, a bottom surface 914 mounted to a carrier 916 by an adhesive layer 918 and TSVs 915 spaced throughout the substrate 910. The grinding process leaves a layer of overburden 920 (e.g., substrate material above the TSVs) that could vary in thickness (i.e., thicker at the edge, uniform across the substrate or thicker at the center of the substrate than at the edge) (within substrate thickness variation). Likewise, there can be a difference in height of the substrate material above the TSVs on a substrate to substrate basis (substrate to substrate thickness variation). These differences in the layer above the TSVs can be greater than the allowable difference in height of the exposed vias. In addition, the adhesive layer can also vary in thickness and uniformity, rendering exterior measurements ineffective at determining the thickness and uniformity of the material remaining in the top silicon substrate, above the end of the via. FIG. 9A also depicts a cross section of an exemplary post etching TSV substrate.

Imaging device measures the actual thickness of the substrate over the surface by optically scanning the substrate. Various methods of optically scanning the substrate to determine thickness information (which can include the substrate's thickness, total thickness variation (TTV, which represents the difference between the minimum and maximum thickness measured on the substrate), substrate flatness (e.g., wafer bow), surface roughness and otherwise analyze the topography of a substrate) are known by those skilled in the art and are suitable for use in the present invention. Preferably, imaging device 600 scans a representative sample of the surface of the substrate and collects thickness information, including preferably, the substrate thickness over the representative sample and transmits the thickness information to process controller 705. The sample size (number of data-points collected over the substrate surface) can be adjusted depending on the level of detail required by the application of the processed substrate, and can range from a detailed scan of the entire surface to just a few data points over the surface. More specifically, thickness measurements can be collected at various locations on a substrate, and the measurements can be used to interpolate the thickness at intermediate locations as a function of the distance between the two data points. In other words, the software of the present invention can perform an interpolation operation for generating such measurements.

Processor 710 executing one or more software modules 730 including, preferably imaging module 770 or database module 778, can also configure the process controller 705 to record the thickness information to storage 790 or memory 720 for further processing as further described herein.

Then at step 820, processor 710 executing one or more of software modules 730, including preferably substrate thickness module 770, configures process controller 705 to determine the radial thickness of the particular substrate and etch depth to identify the radially defined areas of the surface of the particular substrate where the substrate is thicker or thinner (e.g., edge heavy, uniform or center heavy) and the amount of material to be removed at a given radius.

Figure 9B:
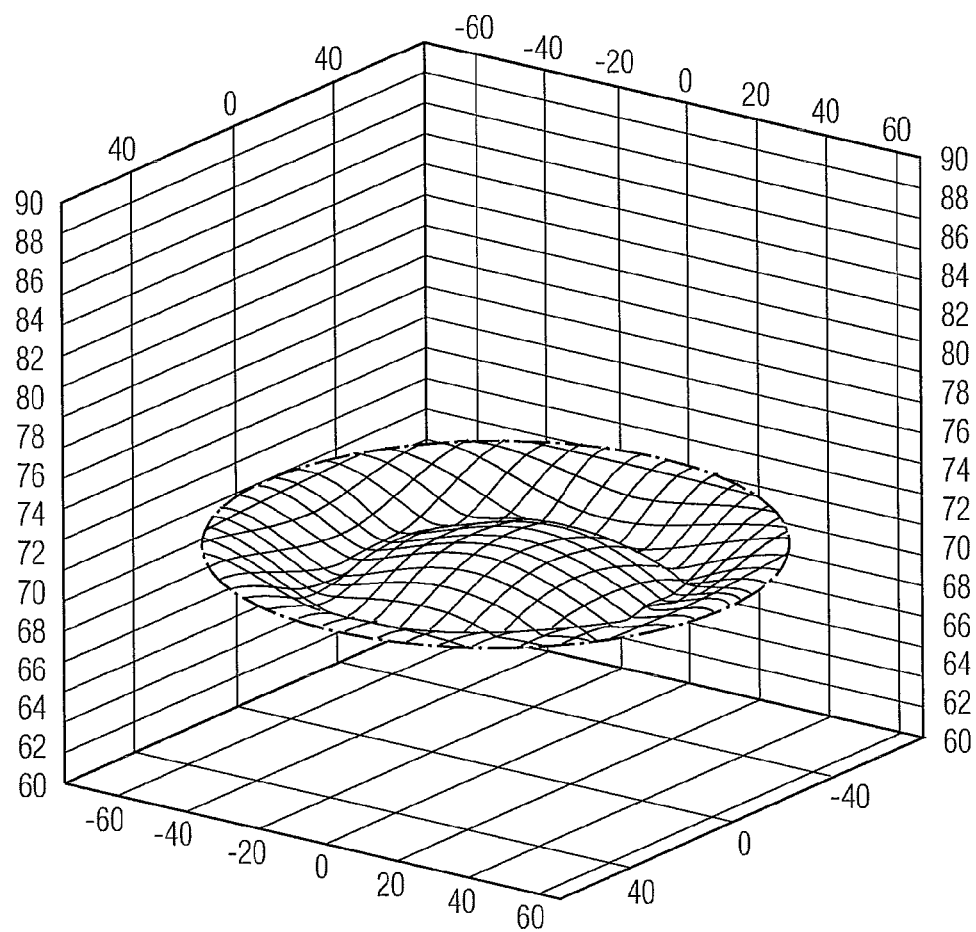
FIG. 9B is a graph showing the radial thickness of an exemplary substrate in accordance with one embodiment disclosed herein.
Figure 9C:
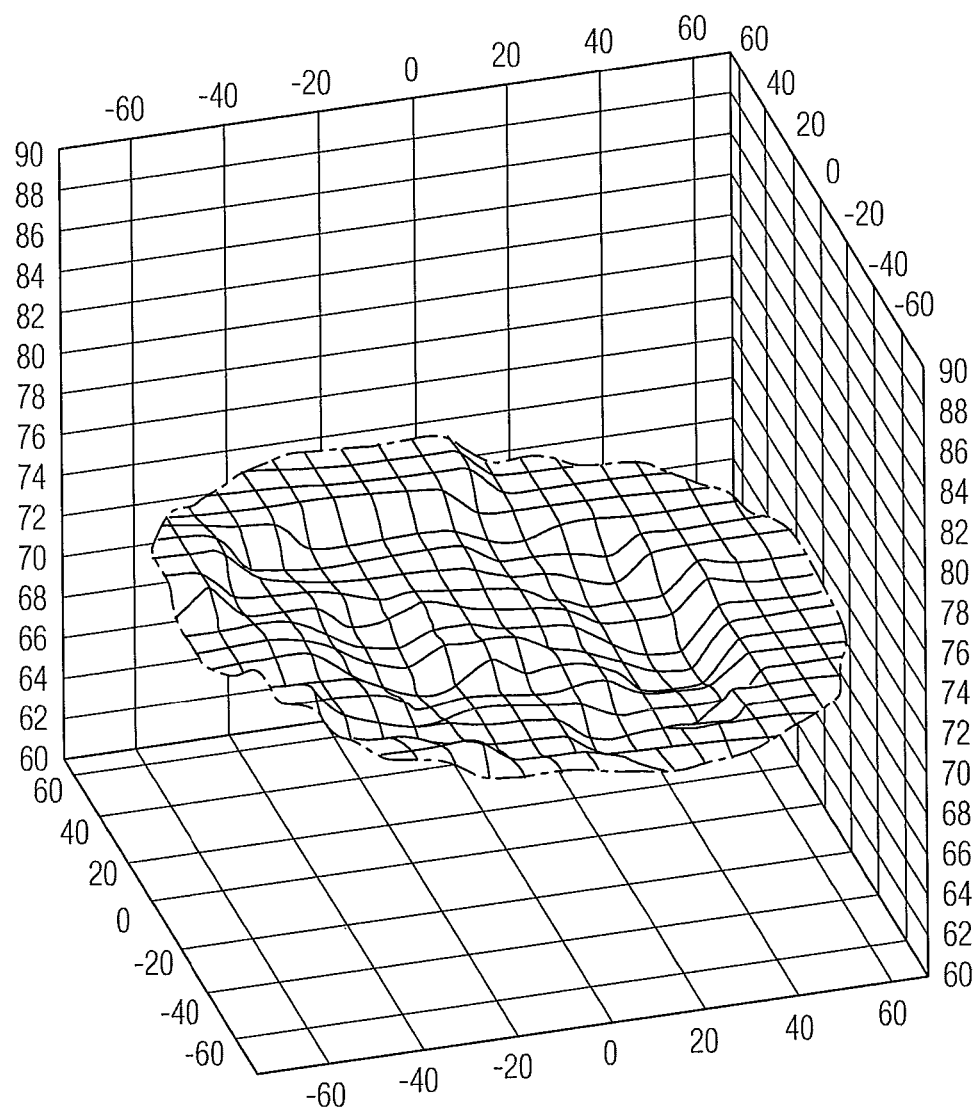
FIG. 9C is a graph showing the thickness of an exemplary substrate in accordance with one embodiment disclosed herein.

Radial thickness is the average thickness of the substrate at a given radius. Similarly, surface uniformity of the particular substrate is a measure of how radial thickness varies across the surface of the wafer. Radial thickness is used to identify radial dependent non-uniformities in thickness i.e., at what radial areas on the surface of the substrate the overburden must be removed more than others. Radial thickness can be calculated according to an algorithm that is a function of the average thickness of the particular substrate measured at step 810 around a given radius of the substrate. FIG. 9B shows a screen shot of a graphical representation or ring map, of the radial thickness of an exemplary substrate that can be generated by the process controller and displayed by display 740. FIG. 9C depicts a graphical representation of the actual thickness over the surface of the exemplary substrate, or surface map.

Etch depth is the desired depth of material to be removed from the surface of the substrate. The method of determining etch depth can vary depending on the type of substrate and intended application of the substrate.

In the case of etching substrates to reveal TSV's, etch depth is the thickness of the overburden between the top surface of the substrate and the top of the TSVs. In addition, etch depth can also be a function of the desired height of the revealed TSVs (TSV reveal height). Preferably, etch depth is determined for a sample of radial locations on the surface of the particular substrate according to an algorithm that subtracts a reference height of the TSVs and desired TSV reveal height from the radial thickness. Accordingly, etch depth is a function of radius and can be adjusted to minimize radial dependent non-uniformities in overburden thickness.

The reference height of the TSVs in the particular substrate can be obtained from the manufacturer of the particular substrate. Alternatively, or in addition, the reference height can also be a function of measurements of the actual height of the TSVs of one or more etched substrates.

In the case of etching non-TSV substrates, for example, a wafer thinning process, etch depth can be calculated as a function of radial thickness and other thickness related information, including TTV (total thickness variation). Accordingly, etch depth can be adjusted to improve the overall thickness uniformity, surface uniformity of the non-TSV substrates being etched.

Then at step 830, processor 710 executing one or more software modules 730, including preferably etch recipe module 778, can configure process controller 705 to generate an etch recipe for the particular substrate that can be executed by the etching apparatus 400 to etch the particular substrate to obtain the desired etch profile.

In general, the etch profile includes etch depth as determined in step 820. Etch profile can also include other changes that need to be made to the particular substrate to achieve the desired physical characteristics including but not limited to surface roughness. Accordingly, etch profile is a function of application dependent physical characteristics of the processed substrate, by example and without limitation, desired surface roughness, desired TSV reveal height, desired substrate thickness, and also a function of actual physical characteristics of the particular substrate including via depths and radial thickness.

For example, in regards to surface roughness, in, say, metal deposition applications a slight surface roughness can improve adhesion, while in substrate bonding applications, a very smooth surface is required.

The etch recipe is generated according to an algorithm which is a function of the etch profile of the particular substrate. The etch recipe consists of a variety of single wafer wet etch process control parameters relating to the radial location on the surface of the particular substrate where material should be removed and the amount of material to remove so as to achieve the desired etch profile.

A variety of parameters can be adjusted to control the radial location on the surface of the substrate where etching is concentrated, including but not limited to the radial position of the etch tool 430 (also referred to as the arm) and nozzle 435 dispensing the chemical etchant onto the substrate, arm scan speed, acceleration, deceleration and nozzle height. It is understood that dispensing an etchant onto a substrate at a particular radial location generally localizes the etching process to that particular radius of the substrate and as such the position and movement of the arm and nozzle controls the location of etching. Arm scan speed is the speed at which the arm and nozzle dispensing the chemical etchant moves from one position on the substrate to another, and acceleration and deceleration is the rate of change of the arm scan speed over a period of time, and the nozzle height is the distance between the nozzle and the substrate.

Figure 9D:
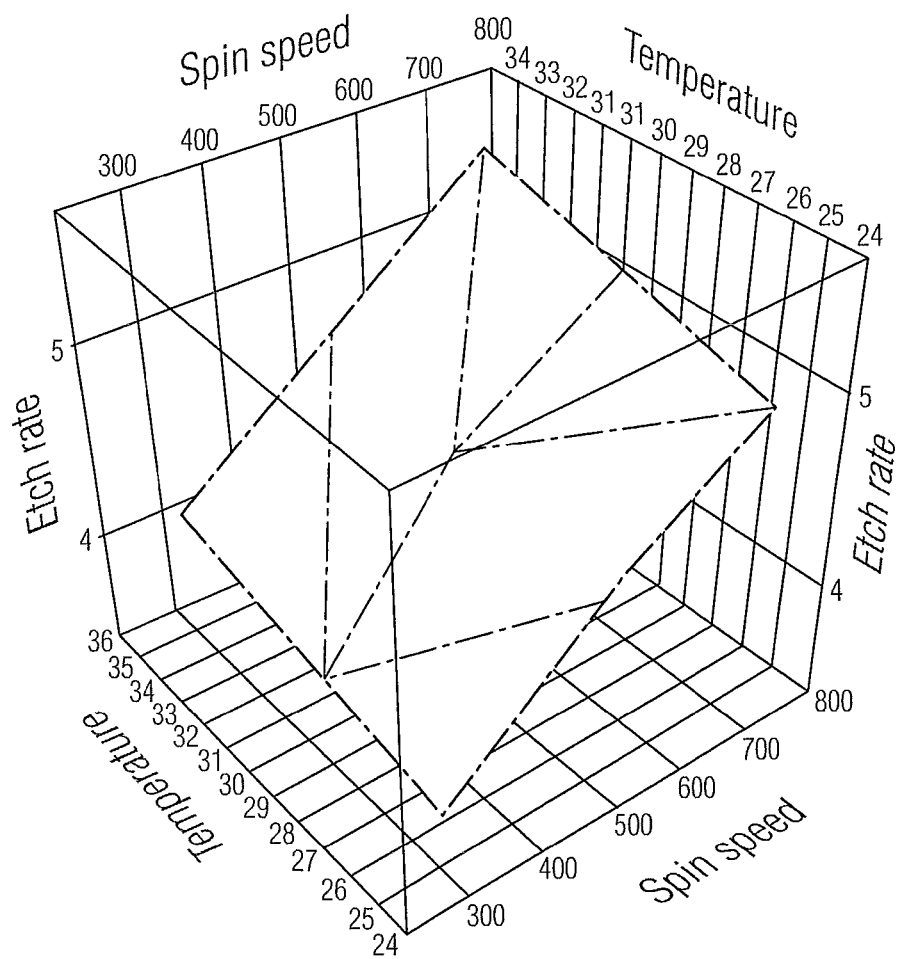
FIG. 9D is a graph showing an exemplary relationship between spin-speed, etch rate and etchant temperature in accordance with one embodiment disclosed herein.

The parameters that can be adjusted to control etch rate (i.e., the rate at which the substrate material is chemically removed), include but are not limited to, the spin speed of the substrate, the concentration of the chemical etchant, the temperature of the chemical etchant, and dwell time. Spin speed is the speed at which the chuck 420 and the substrate thereon are spinning while chemical etchant is being deposited on the substrate surface. FIG. 9D is an exemplary graph of silicon etch rate as a function of temperature of the chemical etchant and spin speed and illustrates the relationship between etch rate and temperature and spin speed.

Figure 9E:
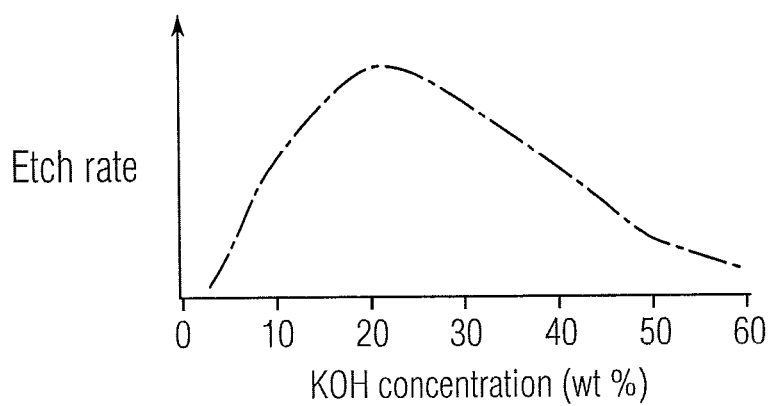
FIG. 9E is a graph showing an exemplary relationship between etch rate and etchant concentration in accordance with one embodiment disclosed herein.

The chemical etchant concentration is the concentration of the chemical etchant that is used to chemically remove the top surface of the substrate. KOH (Potassium Hydroxide) is one exemplary etchant typically used to etch silicon TSV substrates because of its property to etch silicon selectively as opposed to conductors (such as Copper) and insulators (such as silicon oxide). FIG. 9E depicts an exemplary graph plotting the relationship of KOH concentration to silicon etch rate.

The parameters that can be adjusted to control the etch uniformity (i.e., the uniformity of the radial thickness of the resulting substrate) include but are not limited to, the spin speed of the substrate and the dwell time of the arm depositing chemical etchant on the radial; locations of the substrate being etched.

Figure 9F:
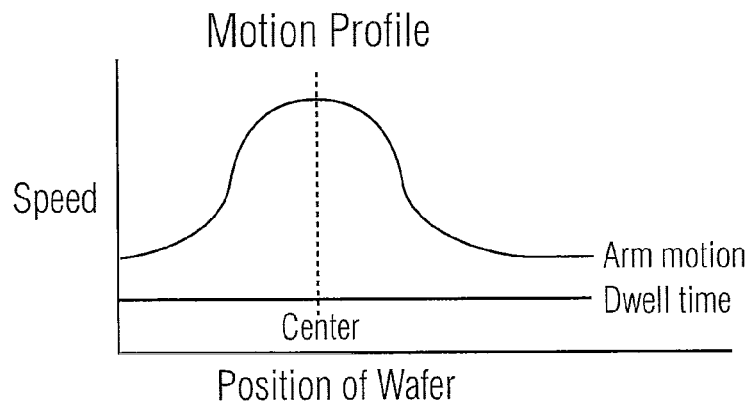
FIG. 9F is a graph showing an exemplary relationship between arm scan speed and dwell time as a function of radial position in accordance with one embodiment disclosed herein.

Dwell time is the amount of time the nozzle is dispensing the etchant on a particular radial portion of the substrate. Increasing dwell time at a particular radius of the substrate causes the substrate to be etched more at that radius. Dwell time can be controlled by adjusting process parameters discussed above such as arm scan speed, acceleration and the spin speed of the chuck. More specifically, due to the circular shape of the substrate that is spinning on the chuck during the etching process, less time is required to deposit the chemical etchant necessary to etch the center of the substrate than the edge of the substrate and as such the speed of the arm, acceleration/deceleration between one radial position to another over the substrate is adjusted to vary the amount of time the etchant is dispensed at a particular location. FIG. 9F is an exemplary graph plotting the arm scan speed as a function of distance from the center of the substrate to achieve a uniform dwell time over the entire surface of the substrate and illustrates the hyperbolic motion profile that can be used to achieve the uniform dwell time. The exemplary hyperbolic motion profile illustrated provides the basis for variations in arm scan speed and acceleration to change the dwell time over a particular location of the substrate as would be understood by those skilled in the art.

Figure 9G:
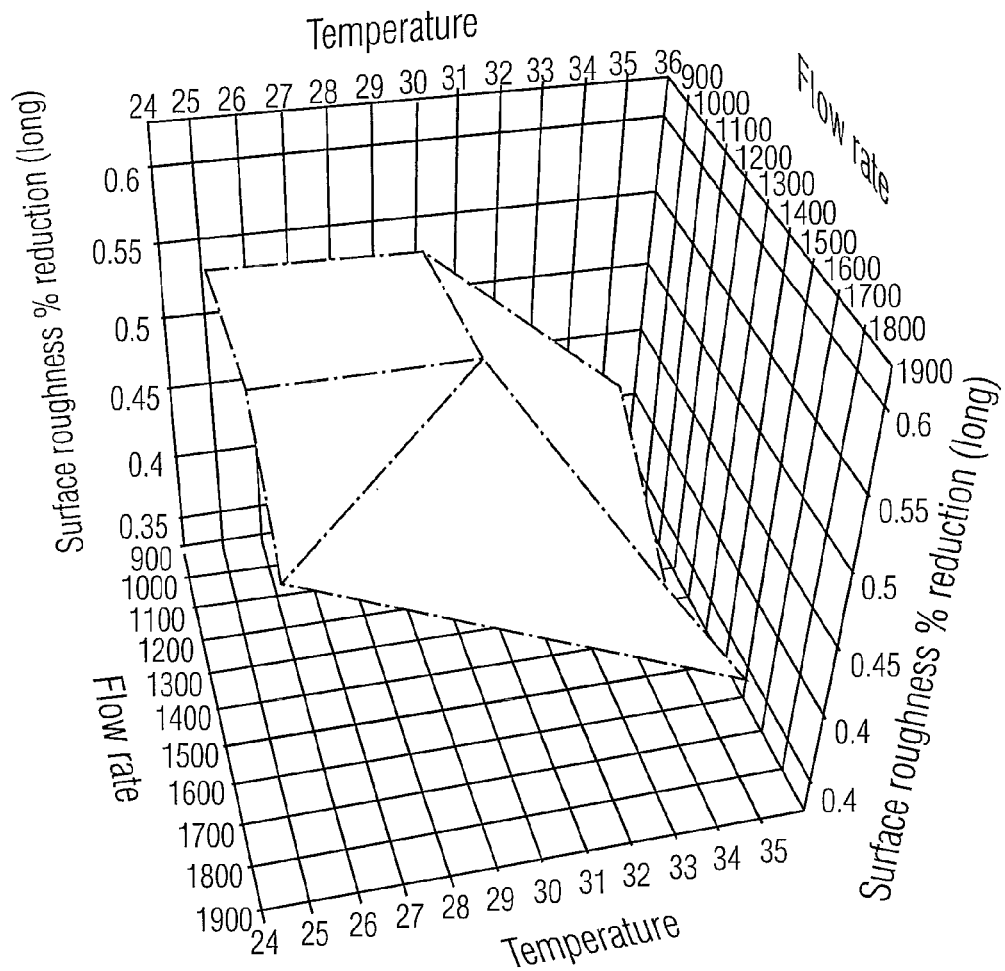
FIG. 9G is a graph showing an exemplary relationship between flow rate and etchant temperature and surface roughness in accordance with one embodiment disclosed herein.

The parameters that can be adjusted to control the surface roughness include but are not limited to, the temperature of the chemical etchant and flow rate of the chemical etchant onto the substrate. FIG. 9G depicts an exemplary graph plotting surface roughness as a function of flow rate and temperature for a silicon TSV substrate etch, and illustrates the proportional relationship of surface roughness and flow rate and temperature.

Returning to FIG. 8, in particular step 830, processor executing one or more software modules 730, including preferably etch recipe module 778, can configure process controller 705 to define one or more of the aforementioned parameters that control etching location, surface roughness, etch rate, dwell time and surface uniformity to generate an etch recipe to selectively etch the overburden in various radial locations on the surface of the particular substrate to achieve the desired etch depth, radial thickness and surface roughness. It should be understood that the parameters can be defined as a function of etching location or other variables and are therefore variable throughout the course of the etching process. For example, in a substrate with a radial thickness that is, say, edge heavy, dwell time can be increased near the edge of the substrate, and spin speed can be decreased to achieve a greater etch depth at the edge.

Additionally, the etch recipe can include an etch duration. Etch duration is the amount of time that the etch process is being performed on the particular substrate and can be varied to control the amount of material that is removed during the etching process. The longer a given etch recipe is executed on a substrate the more substrate is removed and as such, the overall thickness is reduced.

Then at step 840, processor 710 executing one or more software modules 730, including preferably etch recipe module 778, can configure process controller 705 to cause the etching apparatus 400 to etch the substrate according to the etch recipe.

Then at step 850, processor 710 executing one or more software modules 730, including preferably cleaning module 770, can configure the process controller 705 to cause the substrate cleaning apparatus 1600 to clean the substrate to eliminate residual etchant and other particles from the surface of the substrate. The cleaning process can include a brush scrub using one or more brushes 1630 and the deposit of a cleaning solution from nozzle 1650. In addition, process controller can cause substrate cleaning apparatus 1700 to perform a final clean process to remove small particles from the substrate surface using one or more nozzles 1750 to dispense a high velocity spray of cleaning solution onto the particular substrate and/or use a megasonic cleaning apparatus 1775. In addition, this final cleaning step can include a drying apparatus 1780 to dry the wafer at the end of the final cleaning process.

Figure 9H:
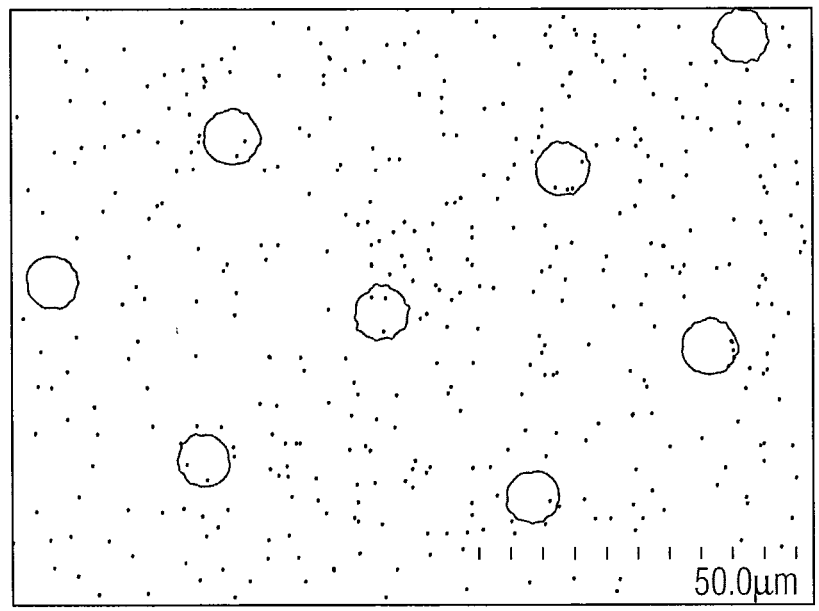
FIG. 9H illustrates an exemplary scanning electron microscope image of a substrate having TSVs in accordance with one embodiment disclosed herein.
Figure 9I:
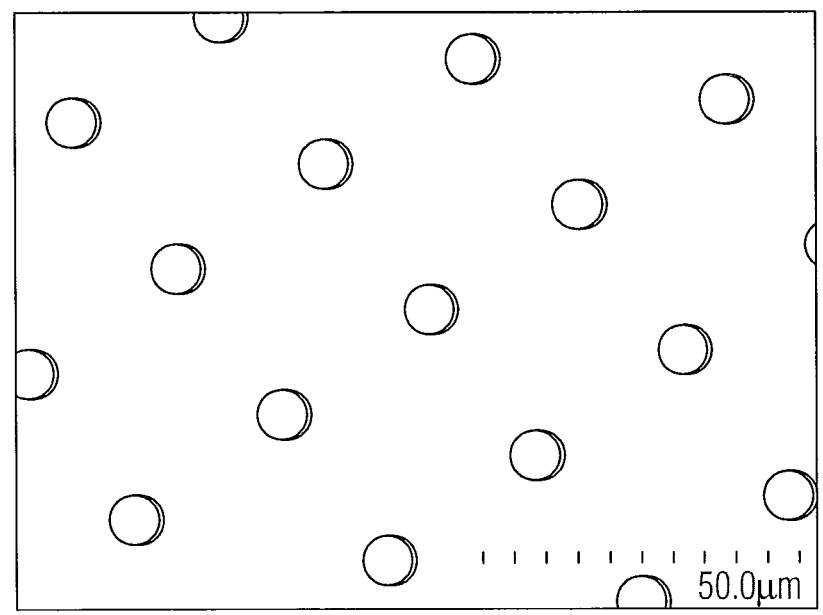
FIG. 9I illustrates an exemplary scanning electron microscope image of a substrate having TSVs in accordance with one embodiment disclosed herein.

For example, after a KOH etch of a silicon TSV substrate, residual potassium based particles and potassium ions remain on the surface of the substrate and will result in a change of electrical properties of the substrate surface that will result in yield loss if not removed. Accordingly, the substrate is cleaned to minimize the amount of residual particles, ions and etchant. FIG. 9H depicts a scanning electron microscope image of an exemplary substrate with revealed TSVs and residual particles and ions prior to the cleaning step. FIG. 9I depicts a scanning electron microscope image of an exemplary substrate with revealed TSVs free of residual particles and ions post cleaning step.

Then at step 860, processor 710 executing one or more software modules 730, including preferably imaging module 770, can configure the process controller 705 to cause the imaging device 600 to measure the thickness of the particular substrate, as discussed in relation to step 810 and transmit the thickness information to process controller 705.

Then returning to and in furtherance of step 820, processor 710 executing one or more software modules 730, including preferably etch recipe module 774, can configure the process controller 705 to analyze the thickness information obtained at step 860 to adjust the etch profile and/or etch recipe for subsequent substrates to undergo the etching process according to the disclosed embodiments. More specifically, the process controller can compare the post-processing thickness information to the pre-processing thickness information to determine whether the etch recipe executed by etching apparatus 400 successfully etched the desired amount of substrate at the desired locations and at the desired etch rate and resulted in a processed substrate having the desired physical characteristics, including surface uniformity. In addition, information about the actual height of the vias can be used to adjust the reference via height as discussed above. As discussed in relation to step 830, depending on the etch rate and thickness information, the process controller can adjust the etch recipes for subsequent substrates, or adjust parameters to maintain a consistent etching environment such as restore the concentration of the chemical etchant and adjust chemical etchant temperature as would be understood by those skilled in the art.

Accordingly, system 100 executing process flow 800 provides a fully automated, production grade, solution that: uses specialized metrology to generate, in real time, etch recipes that are specifically tailored to each substrate being etched and based on previously etched substrates; and etches the substrates using a single wafer wet etch apparatus. As a result, the system can achieve a precise etch depth, surface uniformity and in general produce higher quality substrates, minimize waste and realize the benefits associated with a single wafer wet etch process.

As mentioned above, the measurement steps and etching steps are all performed as part of an integrated system defined by complementary devices that are located within a single housing.

According to yet another salient aspect of the invention, the etching process described in relation to step 840 can include an end-point detection device 500 that is used to more accurately determine the point at which the TSVs are exposed and more accurately control the length of the etching process (duration) and the exposed height of the TSVs. As discussed above, the etching device 400 can include an end-point detection device 500 which is an in situ process monitoring system that includes preferably an light emitter 510 and a charge coupled device (CCD) light detector (or other type of detector) 520. The emitter, which is preferably a high intensity light emitter, emits the light on at least a portion of the substrate while within the etch chamber 410 undergoing the etching process and the CCD detects the light reflected off of the substrate. Generally, the nature of the light reflected off the substrate surface and collected by the CCD, the light signature, will vary depending on the composition of the surface. Accordingly, the light reflected by a substrate surface having an overburden will have different properties, or light signature, than the light reflected by a substrate having revealed TSVs. The process monitoring system (e.g., process controller 705 and the like) monitors the detected light signature to identify the point at which the light signature is comparable to a reference signature for a substrate having revealed TSVs. In other words, the detected light signature is analyzed to determine when the substrate has a detected light signature that is indicative of a substrate having revealed TSVs, thereby indicating that the etching process is complete, or nearly complete, and revealed TSVs are present.

Figure 10:
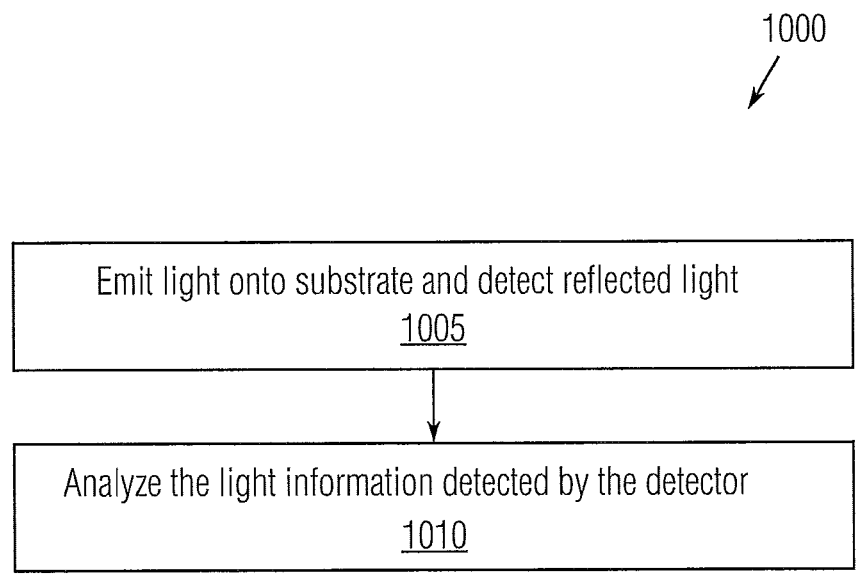
FIG. 10 is a flow diagram illustrating a routine for performing a wet etching process in accordance with at least one embodiment disclosed herein.

Turning now to FIG. 10, a flow diagram illustrates a routine 1000 for detecting the point in which TSVs as revealed during the wet etching process step 840 in accordance with at least one embodiment disclosed herein. It should be appreciated that more or fewer operations can be performed than shown in the figures and described herein. These operations can also be performed in a different order than those described herein.

The process begins at step 1005, where processor 710 executing one or more of software modules 730, including, preferably end point detection module 772, configures process controller 705 to cause light emitter 510 to emit light onto at least a portion of the surface of the particular substrate (sample area) and cause the light detector 520 to detect the color of the light being reflected by the portion of the particular substrate. Preferably, the light detector is a CCD detector, although other alternative light detectors can be used. The detector transmits the detected reflected light information to the process controller as further described herein. When etching substrates to reveal TSVs, insufficient light is reflected by the short, thin exposed TSVs at the end of the process under ambient light. According to salient aspects of the disclosed embodiments, high intensity LED and\or colored high intensity light is directed at the substrate to enhance the light signature reflected by the substrate. The light signature includes the intensity of one or more particular wavelengths of light that are detected and monitored by the process controller. For example, in detecting the reveal point of TSVs in a silicon wafer, the light signature can include three wavelengths of light (blue, red and green). The emitter and/or detector can include one or more light filters such as a red light filter to adjust the characteristics of the light emitted and/or detected. The sample area of the particular substrate that is being monitored by the end point detection device can be one or more points on the surface and can be defined by the process controller by default or by the user. The plurality of points can each correspond to one or more pixels of the CCD detector and the detected reflected light can be averaged to reduce variations due to noise and distortion from the fluid layer on the substrate. The averaged intensity information can be recorded by the process controller and can also be plotted on a chart and displayed on display.

Then at step 1010, processor 710 executing one or more of software modules 730, including, preferably end point detection module 772, configures process controller 705 to analyze the light information detected by the CCD detector to compare the light signature of the particular substrate being etched, as detected by the CCD, to a reference light signature.

It should be understood that at some point prior to etching the particular substrate and/or subsequent substrates, processor executing one or more software modules including, preferably end point detection module, can configure the process controller to determine a reference light intensity by etching a reference substrate for a set duration and analyzing frames of information collected by the CCD at specified intervals during the etching process and calculate the intensity of three wavelengths of light (blue, red and green) at each frame and noting the intensity of the three wavelengths of light when the TSVs are known to be revealed. The process controller can also plot the light intensity data for the reference substrate over time and display the plot to a technician. The change in the light signature should be similar for subsequent substrates that are run, provided that subsequent substrates have similar physical properties (e.g., substrate composition and size and TSV composition and size), as would be understood by those skilled in the art. It should also be understood that the particular rate of change of the light signature can vary depending on the particular etch recipe.

In regards to determining the end point while etching the particular substrate and subsequent substrates, the process controller can detect when the reveal point is reached by analyzing frames of reflected light intensity information collected by the CCD at specified intervals during the etching process and calculate the intensity of three wavelengths of light (blue, red and green) at each frame and compare the light intensity information to the reference light intensity information obtained from the reference substrate. When the light intensity information of the particular substrate corresponds to the reference light intensity information the process controller can end the etching process or begin the over etch stage.

Based on light intensity data, etch rate and initial and final thickness information for the reference substrate, the system can adjust the etch recipe (as described in relation to Process flow 800) for the subsequent substrate and other parameters including but not limited to setting a minimum duration, a maximum duration, the light intensity at the point where TSVs are revealed, and end point of the etch process. The end point can be defined as an over etch duration (e.g., how long the etch process should continue after reveal point is detected), in terms of seconds or percentage of process time in order to reveal the TSVs to a desired height.

For example, when a reference substrate is run, the etch rate is identified to be 2 um/min and the light intensity is detected to be a first value when the TSVs are first revealed. Assuming the average etch depth for a subsequent substrate is say, 10 um (this simplified example is discussed in terms of average etch depth since there may exist radial thickness variations as described above) and the desired TSV reveal height is 2 um, the system can determine that the etch time for the subsequent run should be approximately 5 minutes, based on reference etch rate and etch depth. When etching the subsequent substrate, once the CCD detects a light intensity having the first value (the target light intensity) reveal point is detected and the end point is set to have an over etch time of 1 minute in order to achieve a 2 um revealed TSV height.

Figure 11:
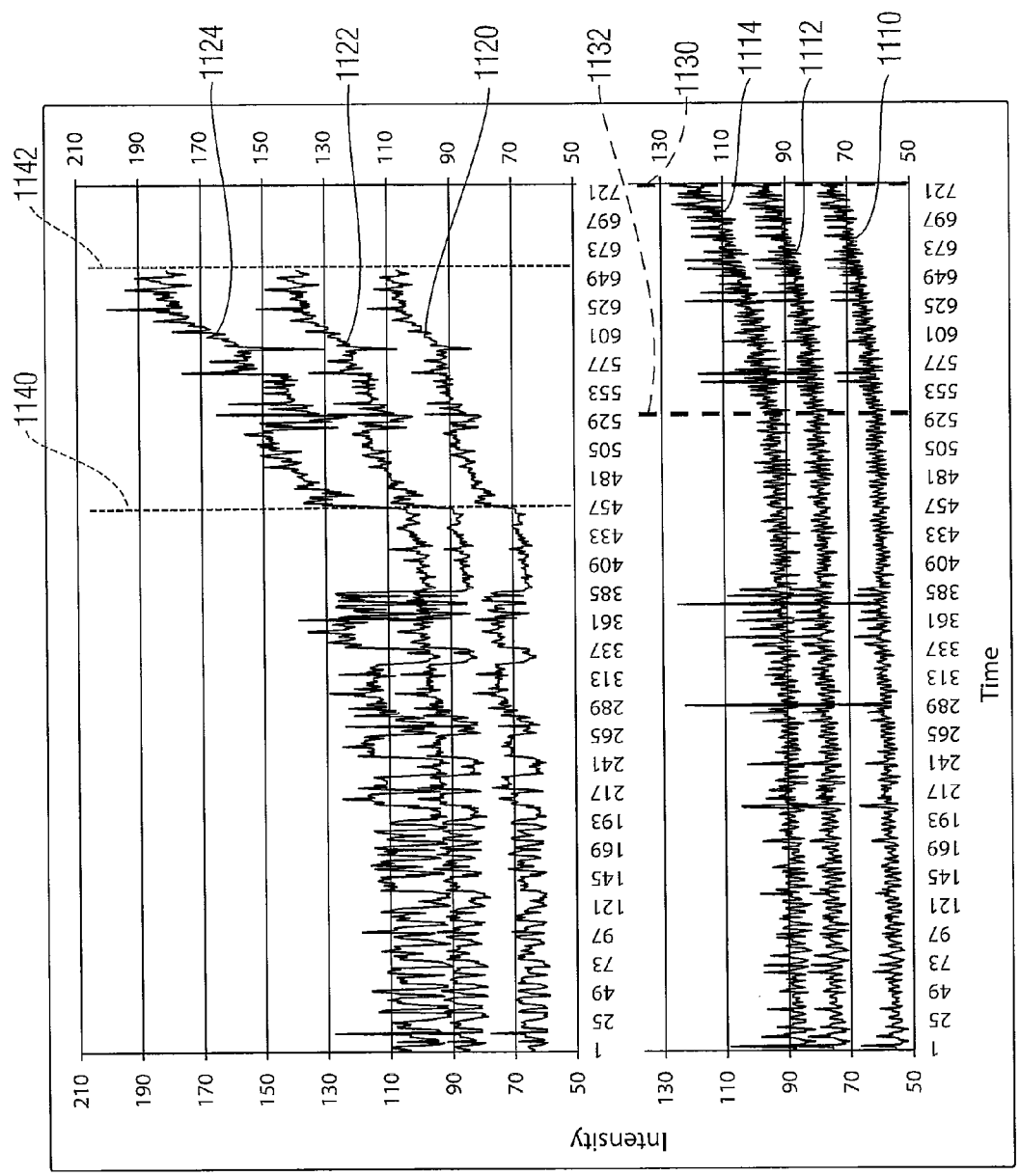
FIG. 11 is a graph showing light intensity values over time in accordance with at least one embodiment disclosed herein.

FIG. 11 depicts an exemplary graph of the light intensity data for the duration of a TSV reveal process according to a disclosed embodiment. The graph depicts light intensity data for the red 1110, blue 1112 and green 1114 wavelengths of light for a reference substrate previously etched. The intensity data is plotted for the duration of the etching process. In this example, the graph depicts the light intensity at the reveal point 1132 of the reference wafer at around t=530 and the end-point 1130 at around t=721. This end point includes the time to expose a portion of the via. The graph also depicts a plot of the light intensity data for the red 1120, blue 1122 and green 1124 wavelengths of light for a particular substrate that has been etched using end point detection according to the light intensity data collected from the reference wafer. The graph shows that in this particular exemplary run, the particular substrate's reveal point 1140 (the point at which the light signature of the particular substrate matches the signature at reference reveal point 1132) occurred at t=457. In addition, based on the reveal point 1140 and etch rate and desired over etch, the actual endpoint for the particular substrate occurred at t=650.

Accordingly, system 100, which includes the single wafer wet etching apparatus 400 that includes an end point detection device 500 and implements the routine 1000 for detecting the point in which TSVs are revealed provides an automated solution to precisely control the TSV reveal height and adjust etch recipe parameters in real time according to feedback concerning previously etched wafers. Accordingly the system results in higher quality processed substrates, minimizes waste and realizes the benefits generally associated with a single wafer wet etch process. Although the wet etching step incorporating end point detection has been described in relation to process flow 800, it should be understood that single wafer wet etching with end point detection can be performed in the absence of one or more of the other steps of process flow 800.

It should be understood that in between each process step discussed in relation to FIG. 8, processor 710 executing one or more of software modules 730 configures process controller 705 to cause wafer transfer device 300 to move the particular wafer between the various stations performing the process steps.

Preferably, throughout the execution of process flow 800 and/or routine 1000, various information and data is collected by the components of system 100, including but not limited to process controller 705, first station 200, second station 210, third station 220, fourth station 230, fifth station 240, and the computer controlled devices or controllers associated therewith including but not limited to wafer transfer device 300, FOUP loadports 160, imaging device 600, etch controller 401, end point detection device 500 and cleaning controller 1601. Processor 710, executing one or more software modules 730, including, database module 780 and display module 780, can configure process controller 705 to collect at least a portion of the data from the various components of system 100, store the collected data in storage 790 and/or memory 720. Furthermore, process controller can display the data on display 740, either in raw form, or manipulated form such as a graphical representation as would be understood by those skilled in the art.

At this juncture, it should be noted that although much of the foregoing description has been directed to a system for performing a wet etching process and methods for wet etching substrates to reveal TSVs, the systems and methods disclosed herein can be similarly deployed and/or implemented in scenarios, situations, and settings far beyond the referenced scenarios. It can be readily appreciated that the system for performing a wet etching process can be effectively employed in practically any scenario in which a substrate is to be etched in a single wafer wet etching station to a desired surface uniformity and thickness.

It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a system, processes and computer implemented control methods, computer system, and computer program product for wet etching substrates. The flowchart and block diagrams in the figures illustrate the architecture, functionality, and operation of possible implementations of systems, methods and computer program products according to various embodiments and arrangements. In this regard, each block in the flowchart or block diagrams as it relates to a computer implemented method can represent a module, segment, or portion of code, which comprises one or more executable instructions for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed:

1. A method for wet etching a substrate using a single wafer wet etching processing system that includes a plurality of stations to produce a substrate having a desired final etch profile, wherein the desired final etch profile defines a desired thickness of the substrate at one or more radial locations on a surface of the substrate after etching, the method comprising the steps of:

measuring, at a measurement station, an initial thickness information for a particular substrate;

calculating an etch profile for the particular substrate including: for each of a plurality of radial locations, calculating a respective etch depth according to the measured initial thickness information for the respective radial location and according to the desired thickness for the radial location after etching, wherein each radial location is a continuous area that surrounds a center of the surface at a respective radial distance from the center, and wherein for each respective radial location, the calculated etch depth is a function of radius at the respective radial location and wherein a first etch depth for a first radial location among the plurality of radial locations differs from a second etch depth for the second radial location among the plurality of radial locations;

generating an etch recipe for selectively etching the particular substrate at each of the plurality of radial locations the respective etch depths, wherein the step of generating the etch recipe includes:

adjusting etch parameters that control the single wafer wet etching apparatus that is located at the etch station and control etching of the particular substrate during the etch step, the etch parameters including a plurality of radial positions of a nozzle dispensing a chemical etchant, and a speed and acceleration of the nozzle between the plurality of positions, and wherein at least the plurality of radial positions are defined to position the nozzle above the first radial location to selectively etch an amount of substrate material defined by the first etch depth from the entire first radial location and subsequently position the nozzle above the second radial location to selectively etch an amount of substrate material defined by the second etch depth from the entire second radial location;

spinning, using the single wafer wet etching apparatus, the particular substrate; and etching, using the single wafer wet etching apparatus that is operating in accordance with the adjusted etch parameters, the particular substrate as it is spun to achieve the desired final etch profile, wherein the etching includes selectively etching the amount of substrate material defined by the first etch depth from the entire first radial location and selectively etching the amount of substrate material defined by the second etch depth from the entire second radial location;

wherein the plurality of stations are disposed within a housing and are accessed by an automated substrate transfer device that is configured to controllably move the substrate between stations.

2. The method of claim 1, further comprising the step of measuring final thickness information at the measurement station for the particular substrate.

3. The method of claim 1 wherein measuring the initial thickness information includes optically scanning one or more portions of each of the plurality of radial locations on the surface of the particular substrate and recording a value of detected thickness as the initial thickness information.

4. The method of claim 1, wherein the initial thickness information includes a value of thickness of the substrate measured at each of the plurality of radial locations on the surface of the substrate, and wherein the desired final etch profile specifies a desired thickness value of the substrate at each of the plurality of radial locations.

5. The method of claim 4, wherein the step of calculating the respective etch depth further comprises subtracting the desired value of thickness for the particular substrate at the respective radial location from the value of thickness measured at the respective radial location.

6. The method of claim 5, wherein the etch depth is also calculated as a function of a reference height of one or more vias filled with conductive material disposed within the particular substrate, wherein the reference height of the one or more vias is measured height of one or more vias of a sample substrate.

7. The method of claim 1, wherein the etch profile for the particular substrate is calculated based on a final thickness information of a previous substrate.

8. The method of claim 1, wherein the step of generating the etch recipe includes adjusting etch parameters as a function of the etch profile.

9. The method of claim 8, wherein the etch parameters control etching of the particular substrate during the etch step by a wet etching apparatus that is located at the etch station, the etch parameters including a position of an arm and a nozzle dispensing a chemical etchant, a spin speed of the particular substrate on a chuck, an arm scan speed, an arm acceleration, a concentration of the chemical etchant, a temperature of the chemical etchant, a dwell time, a flow rate of the chemical etchant and an etch duration.

10. The method of claim 1, wherein the step of etching the particular substrate includes dispensing a chemical etchant onto the surface of the substrate according to the etch recipe by a single wafer wet etching device that is located at the etch station.

11. The method of claim 1, further comprising the step of measuring, in real-time, final thickness information at the measurement station for the particular substrate after etching the substrate and in the event that the desired final etch profile has not been achieved based on the measured final thickness information, then the substrate is delivered back to the etch station by the automated substrate transfer device.

12. The method of claim 1, further comprising the step of cleaning the particular substrate including dispensing a cleaning solution onto the particular substrate and scrubbing the particular substrate.

13. The method of claim 12, wherein the cleaning step includes megasonically cleaning the particular substrate.

14. The method of claim 1, further comprising a step of cleaning the particular substrate including dispensing a cleaning solution onto the particular substrate.

15. The method of claim 1, wherein the step of etching the particular substrate includes detecting the end point in which one or more TSVs are revealed using an end point detection device.

16. The method of claim 1, wherein calculating the etch profile further comprises: calculating an etch rate based on the etch rate from a previous substrate.

17. The method of claim 1, wherein the etch parameters include a plurality of nozzle heights and during the step of etching the particular substrate, a height of the nozzle is adjusted so that the nozzle assumes one of the plurality of nozzle heights, wherein the nozzle height is a distance between the nozzle and the substrate.

* * * * *